United States Patent [19]

Kikuchi et al.

[11] Patent Number: 4,741,348
[45] Date of Patent: May 3, 1988

[54] HEATING APPARATUS FOR HYPERTHERMIA

[75] Inventors: Makoto Kikuchi, 16-19, Inokashira 1-chome, Mitaka-shi, Tokyo; Shinsaku Mori, 31-6, Okusawa 1-chome,, Setagaya-ku, Tokyo; Yoshio Nikawa, 26-14, Nerima 2-chome, Nerima-ku, Tokyo; Takashige Terakawa, c/o. Tokyo Keiki Co. Ltd., 16-46, Minamikamata 2-chome, Ohta-ku, Tokyo, all of Japan

[73] Assignees: Tokyo Keiki Co., Ltd.; Kikuchi, Makoto; Shinsaku Mori; Yoshio Nikawa, all of Tokyo, Japan

[21] Appl. No.: 759,307

[22] Filed: Jul. 26, 1985

[30] Foreign Application Priority Data

Jul. 31, 1984 [JP] Japan .................. 59-162468
Jul. 31, 1984 [JP] Japan .................. 59-162469
Jul. 31, 1984 [JP] Japan .................. 59-162470

[51] Int. Cl.[4] ............................................. A61N 5/00
[52] U.S. Cl. ............................ 128/804; 219/10.55 R; 219/10.55 F
[58] Field of Search ............ 128/804, 399-402, 128/421-423 R; 219/10.55 R, 10.55 A, 10.55 B, 10.55 F

[56] References Cited

U.S. PATENT DOCUMENTS

| | | | |
|---|---|---|---|
| 3,077,195 | 5/1963 | Folsche | 128/804 |
| 4,108,147 | 8/1978 | Kantor | 128/804 |
| 4,140,130 | 2/1979 | Storm, III | 128/804 |
| 4,204,549 | 5/1980 | Paglione | 128/784 |
| 4,228,809 | 10/1980 | Paglione | 128/804 |
| 4,282,887 | 8/1981 | Sterzer | 128/804 |
| 4,341,227 | 7/1982 | Turner | 128/804 |
| 4,397,313 | 8/1983 | Vaguine | 128/804 |
| 4,397,314 | 8/1983 | Vaguine | 128/804 |
| 4,403,618 | 9/1983 | Turner et al. | 128/804 |
| 4,446,874 | 5/1984 | Vaguine | 128/804 |
| 4,462,412 | 7/1984 | Turner | 128/804 |
| 4,530,358 | 7/1985 | Forssmann | 128/328 |
| 4,586,516 | 5/1986 | Turner | 128/804 |
| 4,589,424 | 5/1986 | Vaguine | 128/804 |

FOREIGN PATENT DOCUMENTS

| | | | |
|---|---|---|---|
| 0111386 | 6/1984 | European Pat. Off. | 128/399 |
| 1440333 | 4/1969 | Fed. Rep. of Germany | 219/10.55 F |
| 2060923 | 7/1971 | Fed. Rep. of Germany | |
| 2648908 | 5/1978 | Fed. Rep. of Germany | |
| 0028338 | 3/1977 | Japan | |

OTHER PUBLICATIONS

Magin, "A Microwave System . . . Animals", IEEE Trans. Microwave Theory & Teh, MTT-27, No. 1, pp. 78-83, Jan. 1979.
Robinson et al, "Techniques for Uniform . . . ", IEEE Trans. Microwave Theory & Tech., MTT 26, No. 8, pp. 546-549, Aug. 1978.
Astrahan et al, "A Localized Current Field . . . ", Med. Phys. 9(3), pp. 419-424, May/Jun. 1982.
The Oct. 1976 issue of Microwaves, article entitled: "Microwaves Score TKO in Fight Against Cancer".
NASA Technical Brief, p. 59, Spring 1980.
"Hyperthermia in Cancer Therapy", by F. Kristian Storm, M.D., G. K. Hall Med Pub. 1983, title page and table of contents.

Primary Examiner—Lee S. Cohen
Attorney, Agent, or Firm—Sandler & Greenblum

[57] ABSTRACT

A heating apparatus for hyperthermia utilizes electromagnetic waves for locally heating cancerous cells within a living body. Electromagnetic waves output from a single electromagnetic wave generating device are branched into a plurality of electromagnetic wave outputs, which are respective employed to conduct hyperthermia treatments for a plurality of patients, the level of each of the branched outputs being adjustable. The whole of the hyperthermia system is controlled in a concentrated fashion from a single section by way of time-division multiplexing. It is therefore possible for a plurality of patients to be subjected to hyperthermia treatment at the same time and in parallel with each other, even when the conditions of these patients differ from one another. Further, it is advantageously possible to simplify the arrangement of the system as a whole and provide an even more precise control of the system.

15 Claims, 23 Drawing Sheets

HEATING APPARATUS FOR HYPERTHERMIA

BACKGROUND OF THE INVENTION

1. Field of the Invention

The present invention relates to a heating apparatus for hyperthermia and, more particularly, to a heating apparatus for hyperthermia which deteriorates the regenerative functions of cancerous cells by heating them with electromagnetic waves, thereby liquidating these cancerous cells.

2. Description of the Prior Art

In recent years, hyperthermia has been given wide attention and papers have been written on hyperthermia, a therapy which deteriorates the regenerative functions of cancerous cells and thereby liquidates significant portions of them by applying heat of approximately 43° C. for one or two hours and repeating the treatment at certain intervals. (MICROWAVES, October, 1976).

There are two kinds of hyperthermia therapy: general and local heating methods. Three methods have been proposed for local heating: one utilizes electromagnetic waves, the second uses electric conduction and the third uses ultrasonic waves.

Researchers have concluded that the optimum temperature for attacking cancerous cells is 43° C. or thereabouts. Temperatures below this will weaken the effects and temperatures above this will damage normal cells. Hyperthermia aims at liquidating cancerous cells without heating normal cells by maintaining the temperature in a confined narrow range.

However, it has been quite difficult when utilizing conventional means to keep the temperature of cancerous cells at approximately 43° C. for one or two hours due to the peculiar functions of a living body. In particular, heating by electromagnetic waves has been put aside for a long time because a significant portion of the electromagnetic waves is absorbed by the body surface and this method is thus unfit for heating regions deep within the body.

In view of the above-described circumstances, the inventors of this invention have previously proposed a heating apparatus for hyperthermia utilizing electromagnetic waves which is provided with function which enables accurate control of the temperature of a given heated region in a living body such that this temperature is maintained at a predetermined value over a certain period of time.

The inventors of the present invention have also previously proposed a heating apparatus for hyperthermia which is provided with a highly accurate heating control function similar to that of the apparatus proposed in the above and which enables a plurality of patients to be subjected to hyperthermia treatment at the same time and in parallel with each other.

However, the above-described apparatus (in the latter proposition) includes as one of its principal constituent elements a plurality of electromagnetic wave generating means and independent electromagnetic wave supply systems which are connected to the respective electromagnetic wave generating means and which are respectively provided for a plurality of patients, and is arranged such that ON/OFF control of electromagnetic waves and the adjustment of electromagnetic wave output are effected for each of the electromagnetic wave supply systems, whereby a plurality of patients are subjected to hyperthermia treatment at the same time and in parallel with each other. In consequence, although it is possible for the primary object to be satisfactorily accomplished, the conventional apparatus disadvantageously involves an increase in the size of the apparatus as a whole and complication of the arrangement thereof, which fact unfavorably leads to an increase in costs and a complicated control operation.

SUMMARY OF THE INVENTION

It is an object of the present invention to provide a heating apparatus for hyperthermia which enables a highly accurate hyperthermia treatment to be applied to a plurality of patients at the same time and in parallel with each other by utilizing electromagnetic waves and permits a reduction in the size of the apparatus as a whole and simplification of the arrangement thereof.

To this end, according to one aspect of the present invention, there is provided, in a heating apparatus for hyperthermia having a single electromagnetic wave generating means and an applicator which irradiates a given hyperthermia treatment region of a living body with electromagnetic waves output from the electromagnetic wave generating means, an improvement characterized by comprising: a variable electromagnetic wave branching means provided between the electromagnetic wave generating means and the applicator and adapted to branch electromagnetic waves output from the electromagnetic wave generating means into a plurality of electromagnetic wave outputs and to enable adjustment of the output level of each of the branched electromagnetic waves; the applicator being connected to each of the output terminals of the variable electromagnetic wave branching means; and a main control unit which controls the output level of each of the electromagnetic waves branched off by the variable electromagnetic wave branching means in accordance with need.

DETAILED DESCRIPTION OF THE PREFERRED EMBODIMENTS

First Embodiment:

A first embodiment of the present invention will be described hereinunder with reference to FIGS. 1 and 3.

Figure 1:
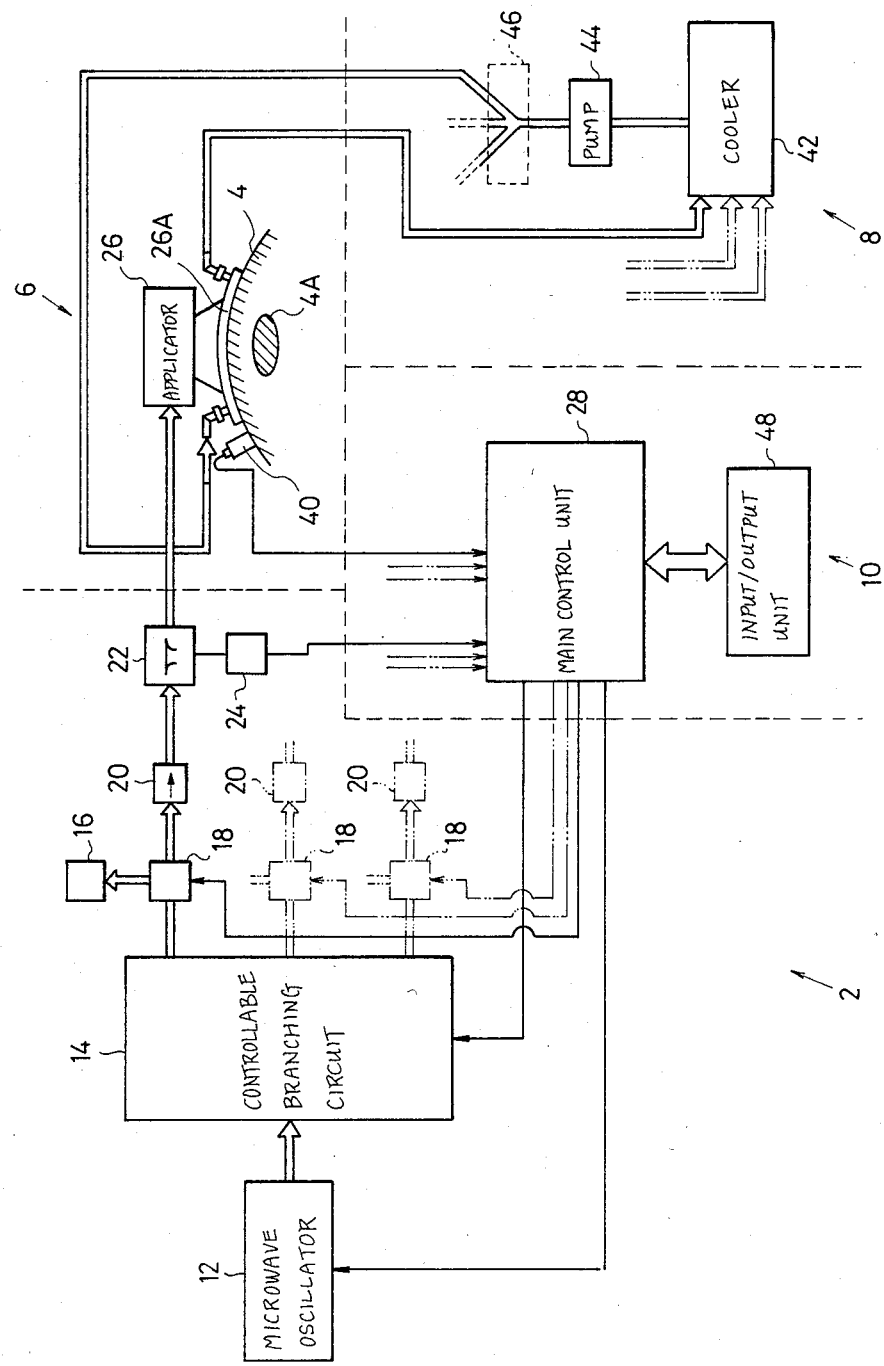
FIG. 1 is a general system diagram of a first embodiment of the present invention.

FIG. 1 is a general system diagram of the first embodiment. In this embodiment, a heating apparatus for hyperthermia includes as its principal elements an electromagnetic wave supply section 2 which generates and supplies electromagnetic waves, an electromagnetic wave irradiating section 6 which irradiates a hyperthermia treatment region (a treatment part which includes cancerous cells 4A as its essential portion) of the body 4 of the corresponding one of the patients with electromagnetic waves supplied from the electromagnetic wave supply section 2, a coolant supply section 8 which supplies a coolant for cooling the surface of the body 4 of each patient at the hyperthermia treatment region, and a control section 10 which performs overall control of the whole of this system.

The electromagnetic wave supply section 2 is composed of: a microwave oscillator 12 serving as an electromagnetic wave generating means which generates microwaves (e.g., 2,450 MHz); a controllable branching circuit 14 serving as a variable electromagnetic wave branching means which branches the microwaves from the microwave oscillator 12 into three directions for three patients (the number of patients assumed is the same throughout the embodiments described hereinafter) and enables control of the output level of each of the branched microwaves; coaxial switches 18 serving as electromagnetic wave switching means each of which enables the supply of the corresponding one of the microwaves branched off by the controllable branching circuit 14 to be switched over between the corresponding electromagnetic wave irradiating section 6 and the corresponding one of the dummy loads 16; and isolators 20 each disposed on the side of the corresponding coaxial switch 18 which is closer to the corresponding electromagnetic wave irradiating section 6 and adapted to prevent any reflected waves from undesirably entering the controllable branching circuit 14; directional couplers 22 each disposed on the side of the corresponding isolator 20 which is closer to the corresponding electromagnetic wave irradiating section 6 and adapted to detect the reflection coefficient of microwaves; and detector circuits 24 each connected to the subsidiary waveguide side of the corresponding one of the directional couplers 22. The microwaves respectively output from the directional couplers 22 are sent to corresponding applicators 26 in the respective electromagnetic wave irradiating sections 6, while the output of each of the detector circuits 24 is delivered to a main control unit 28 in the control section 10.

The controllable branching circuit 14 will now be described in detail with reference to FIGS. 2 and 3.

Figure 2:
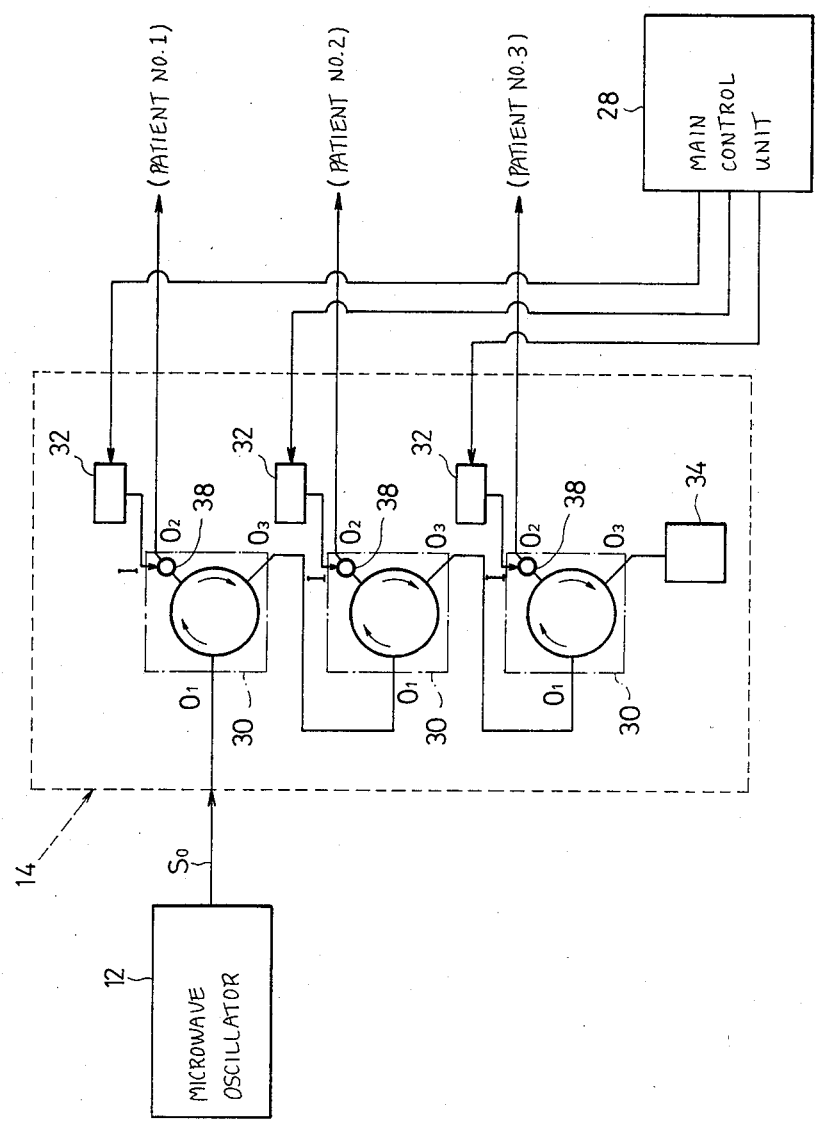
FIG. 2 is block diagram which schematically shows the arrangement of a controllable branching circuit in the embodiment illustrated in FIG. 1.

The controllable branching circuit 14 is composed of three microwave power dividers 30 corresponding to the respective patients, variable voltage sources 32 respectively provided for the dividers 30, and a dummy load 34 connected to the final-stage divider 30, these elements being connected in a manner such as that shown in FIG. 2.

Figure 3:
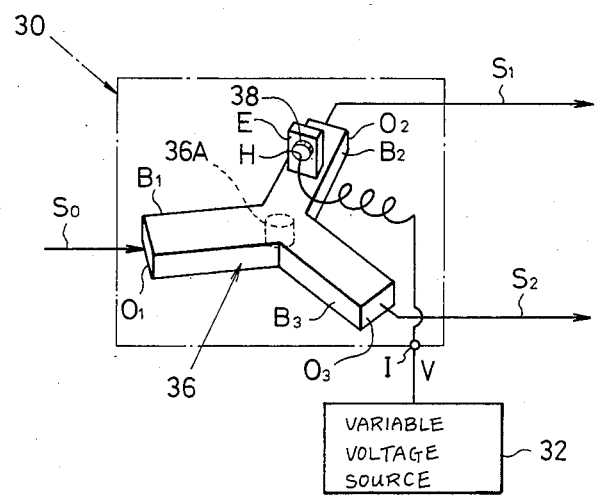
FIG. 3 schematically shows a microwave power divider in the controllable branching circuit illustrated in FIG. 2.

The microwave power dividers 30 have the same arrangement as each other, which is schematically shown in FIG. 3. The microwave power divider 30 shown in FIG. 3 includes as its essential portion a branching-type circulator 36 which is per se known. In this case, the circulator 36 has, as is generally known, at its center a ferrite post 36A which constitutes the circulation center and three (for example) microwave transmission paths $B_1$, $B_2$ and $B_3$ extending radially from the circulation center. Assuming now that the respective free ends of the transmission paths $B_1$, $B_2$ and $B_3$ are represented by openings $O_1$, $O_2$ and $O_3$, microwaves which are supplied from the opening $O_1$ are passed through the transmission path $B_1$ and the circulation center and are further transmitted to the opening $O_2$ through the transmission path $B_2$, while microwaves which are supplied from the opening $O_2$ are passed through the transmission paths $B_2$ and $B_3$ and transmitted to the opening $O_3$. Further, microwaves which are supplied from the opening $O_3$ are transmitted to the opening $O_1$ in a manner similar to the above. Thus, the openings $O_1$ and $O_2$, the openings $O_2$ and $O_3$, and the openings $O_3$ and $O_1$ respectively pair with each other. Each of the branching-type circulators 36 has a branch path E extending outwardly from an intermediate portion of the transmission path $B_2$ and having its free end closed. The branch path E is provided therein with a voltage-dependent variable impedance element 38, for example, a PIN diode or a varactor diode.

Accordingly, in the microwave power divider 30, if microwaves are supplied from the opening $O_1$ of the circulator 36, reflected waves are generated relative to the supplied microwaves within the transmission path $B_2$ at the position where the branch path E extends therefrom. In consequence, when a microwave $S_0$ is input to the opening $O_1$, one portion ($S_1$) of the microwave $S_0$ reaches the opening $O_2$, while the other portion ($S_2$) is led to the transmission path $B_3$. Thus, the microwave supplied to the opening $O_1$ is divided into two portions which are respectively transmitted to the openings $O_2$ and $O_3$. Moreover, the dividing ratio between two microwave powers thus divided changes in accordance with the value of impedance of the voltage-dependent variable impedance element 38 disposed in the branch path E.

On the other hand, a power supply terminal H for suppling electric power to the voltage-dependent variable impedance element 38 is disposed on a side plate portion of the branch path E of the circulator 36 which constitutes each of the microwave power dividers 30. The power supply terminal H is connected to an external control terminal I of the divider 30. The control terminal I is supplied with a voltage V from the corresponding one of the variable power sources 32 for controlling the microwave power dividing ratio.

In this embodiment, three microwave power dividers 30, arranged as above, are series-connected in three stages, as shown in FIG. 2, thereby respectively constituting branched microwave paths of the controllable branching circuit 14. More specifically, the opening $O_1$ of the first-stage divider 30 is connected to the microwave oscillator 12, and the opening $O_3$ of the first-stage divider 30 is connected to the opening $O_1$ of the second-stage divider 30. The opening $O_3$ of the second-stage divider 30 is connected to the opening $O_1$ of the third-stage divider 30, and the opening $O_3$ of the third-stage divider 30 is connected to the dummy load 34. The opening $O_2$ of each of the dividers 30 is connected to the corresponding applicator 26, and each variable impedance element 38 is connected to the corresponding variable power source 32. The dummy load 34 is matched with an actual load in order to prevent any reflection in the final-stage divider 30.

Assuming now that the respective reflection coefficients of the first-, second- and third-stage variable impedance elements 38 are represented by $r_1$, $r_2$ and $r_3$ and the microwave output from the microwave oscillator 12 is denoted by $P_0$, microwaves respectively having the following powers are supplied from the respective openings $O_2$, that is, the respective branched output terminals of the controllable branching circuit 14 to the corresponding applicators 26:

$$\left. \begin{array}{l} (1 - r_1)^2 \cdot P_0 \\ (1 - r_2)^2 \cdot r_1{}^2 \cdot P_0 \\ (1 - r_3)^2 \cdot r_1{}^2 \cdot r_2{}^2 \cdot P_0 \end{array} \right\} \quad (1)$$

Accordingly, by adjusting each variable voltage source 32 such as to control the value for the voltage V supplied therefrom the impedance, that is, the above-described reflection coefficient of the corresponding variable impedance element 38 is changed, whereby the ratio between the microwave outputs divided in each of the divider 30 is changed from zero to infinity. In consequence, it is possible to adjust as desired the microwave power supplied to each of the applicators 26 by individually controlling each of the variable voltage sources 32 of the microwave power dividers 30 connected in three stages.

On the other hand, each of the directional couplers 22 takes out incident and reflected waves while isolating them from each other. Each of the isolated waves is detected and converted into a voltage by the corresponding detector circuit 24 before being delivered to the main control unit 28. The main control unit 28 obtains, for example, a reflection coefficient for each microwave path and calculates a microwave power which is effectively supplied to the corresponding applicator 26. The result of this calculation is employed for adjustment of the microwave power, as will be described later.

Accordingly, the microwaves supplied from the microwave oscillator 12 are branched off by the controllable branching circuit 14 while being adjusted to predetermined output levels as described later. In the case where one coaxial switch 18 has been switched over to the position for supplying microwaves to the corresponding applicator 26, the microwaves passing through this route contribute to the hyperthermia treatment, while in the case where this coaxial switch 18 has been switched over to the corresponding dummy load 16, the microwaves are supplied to this dummy load 16, which has been matched with the actual load, and, therefore, the heating is suspended. These control operations are effected in accordance with instructions from the control section 10.

Figure 4:
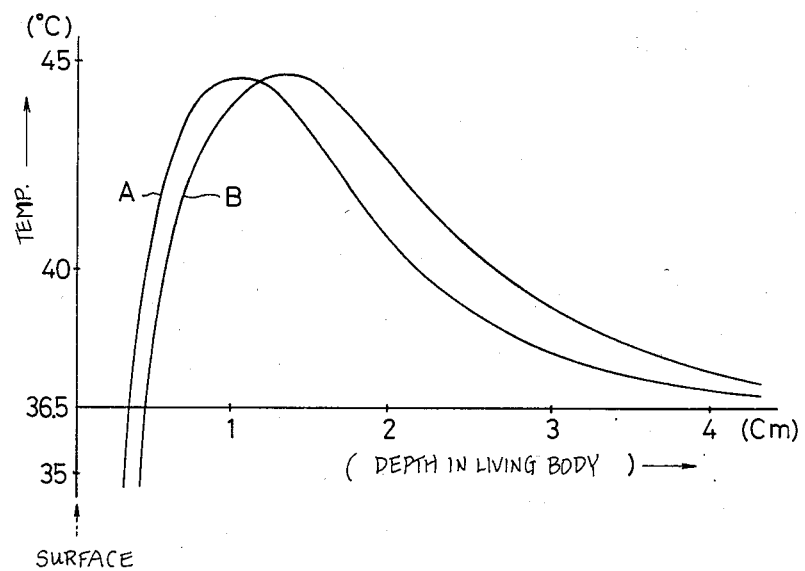
FIGS. 4 and 5 are graphs which show temperature distribution with respect to depth below the skin of a living body.
Figure 5:
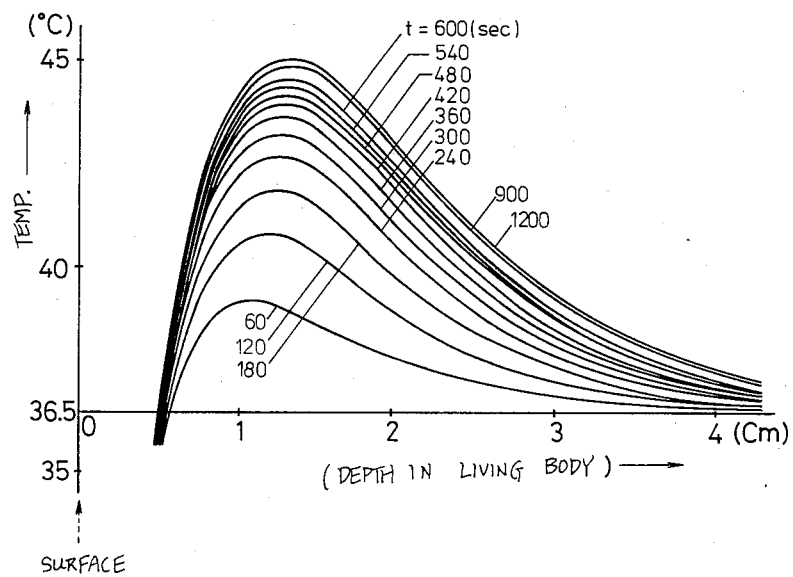

The reason why the output level of microwaves applied to each of the bodies 4 is variably controlled by the above-described arrangement in this embodiment is that it is necessary to adjust the output level of microwaves in accordance with the depth below the skin of the cancerous cells within the body of the patient concerned as described hereinafter. Namely, as the microwave output is increased (that is, the variable impedance is decreased) the temperature peak in heating is shifted toward the surface of a body, whereas as the microwave output is decreased (that is, the variable impedance is increased) the temperature peak is shifted toward the inside of the body since in such a case the heat gradually penetrates into the body. It is therefore necessary for the microwave output level to be set at a value which is suitable to the patient concerned. FIG. 4 is a graph which represents the results of experiments carried out on a phantom model which approximated to a living body. The graph shows comparison between a temperature distribution (A) obtained by irradiating the phantom model with a microwave of 2,450 MHz on the basis of a reference quantity, and a temperature distribution (B) obtained by irradiating the phantom model with a microwave whose output was set by subtracting 3 dB from that reference quantity. Such a frequency band is highest in the frequency regions for hyperthermia and consequently the range of temperature peaks is limited to the surface layer of the phantom model. It may nevertheless be understood that the temperature distribution (B) has a temperature peak at a portion which is about 0.25 cm deeper than that of the temperature distribution (A). However, a reduction in the microwave output requires a corresponding increase in the time taken to heat cancerous cells up to a target temperature. FIG. 5 is a graph which shows changes in temperature of a heated region measured for each predetermined period of time. The curves in the graph represent heating characteristics in this embodiment.

The electromagnetic wave irradiating sections 6 are disposed such as to correspond to the three systems of the branched outputs from the electromagnetic wave supply section 2. Each of the electromagnetic wave irradiating section 6 has an applicator 26 which irradiates the body 4 of the corresponding patient with microwaves, and a cooling mechanism 26A provided on the applicator 26 and brought into contact with the surface of the body 4 to cool the body surface. Each of the cooling mechanisms 26A is recirculatingly supplied with a coolant (water is employed in this case; the same is the case with each of the embodiments described hereinafter) from the coolant supply section 8 which will be described later, whereby the body surface is cooled. In FIG. 1, the reference numeral 40 denotes a cancerous cell temperature sensor serving as a heated region temperature detecting means which is stuck into the cancerous cells 4A within the body 4 of each patient and adapted to detect the temperature of the cancerous cells 4A (referred to simply as the "cancerous cell temperature", hereinafter). Information thus detected is delivered to the control section 10 as illustrated.

Figure 6:
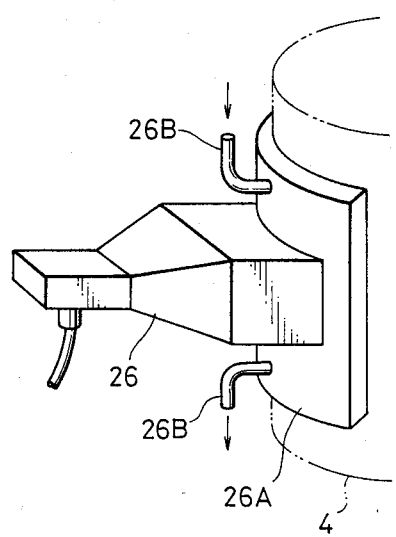
FIG. 6 is a perspective view of one example of an applicator.

One example of the applicator 26 is shown in FIG. 6. As will be clear from the Figure, the applicator 26 is an antenna which is brought into close contact with the surface of the body 4 and irradiates the body 4 with electromagnetic waves for the purpose of heating targeted cancerous cells 4A (see FIG. 1). The cooling mechanism 26A is provided in order to prevent the skin of the body 4 from being thermally burnt which would be caused by the heat generated as the result of dielectric losses in the skin at the area of contact of the body 4 during the heating operation. For this purpose, the cooling mechanism 26A is supplied with water which is forcedly recirculated through a water circulating pipe 26B, thereby cooling the opening side of the applicator 26, that is, the body surface at the hyperthermia treatment region.

The coolant supply section 8 further includes a cooler 42 for cooling the water down to a predetermined temperature, a pump 44 for recirculating the water cooled by the cooler 42, and a coolant distributor 46 which distributes the cooled water to the respective cooling mechanisms 26A of the applicators 26.

On the other hand, the control section 10 is composed of: an input/output unit 48 to which information is input by an operator and which informs the operator of treatment conditions; and a main control unit 28 which constitutes the center of this system and both controls and manages input/output devices and the like in accordance with programs and data respectively stored in program and data memory devices. The main control unit 28 is, as shown in FIG. 1, arranged such as to be fed with information detected by each of the cancerous cell temperature sensors 40 and that detected by each of the directional couplers 22 and to actuate the coaxial switches 18 and the microwave oscillator 12 in the electromagnetic wave supply section 2.

Thus, the main control unit 28 receives through an A/D (analog-to-digital) converter (not shown) the pieces of information respectively obtained by the cancerous cell temperature sensor 40 inserted into the respective bodies 4 of the three patients and those obtained by the directional couplers 22 while successively interchanging them with each other by means of a multiplexer (not shown) provided in the main control unit 28. On the basis of the thus input information and the information which is delivered from the input/output unit 48 instructed by the operator, the main control unit 28 effects judgements and controls so that the cancerous cell temperature is maintained at a desired value. More specifically, the main control unit 28 controls each of the variable impedance elements 38 in the controllable branching circuit 14 and the switching operation of each of the coaxial switches 18 by outputting information via a D/A converter (digital-to-analog) converter (not shown) while successively interchanging each piece of output information with the others by means of a multiplexer (not shown). In addition, the main control unit 28 delivers the various above-described information to the input/output unit 48 in order to apprise the operator of the heating conditions of each body 4. In this case, employment of the multiplexers makes it possible for a single A/D converter and a single D/A converter to process input and output information, respectively.

In the system diagram of FIG. 1, illustration of the portions of the arrangement provided for the other two patients is omitted for the purpose of simplification of the drawing (the same is the case with each of the embodiments described hereinafter).

The following is a description of the operation of the first embodiment.

The time-division multiplexing which is carried out in the main control unit 28 will first be explained with reference to FIG. 7.

In this embodiment, heating control for each individual patient (described later) is effected by time-division multiplexing in synchronism with clock pulses generated in the main control unit 28 in a manner such as that shown in FIG. 7.

More specifically, when a clock pulse (e.g., 1) is input, the control shown in FIG. 9 (described later) is processed within a very short period of time, that is, $\Delta h$ shown in FIG. 7, and a value for the variable impedance $Z_i$ and the switching operation of the coaxial switch 18 for a subsequent microwave irradiation period are determined by the judgement made by the main control unit 28 which functions in response to the control shown in FIG. 9. After microwave irradiation has been effected in accordance with the control for a predetermined time (e.g., H in FIG. 7) (there are, as a matter of course, cases where the judgement made by the main control unit 28 is that no microwave irradiation is to be carried out), the processing of the control shown in FIG. 9 is executed again in synchronism with a subsequent clock pulse 1. Thus, treatment for a single patient is carried out through a series of processings in this way. As regards the other two patients, the heating control is processed in synchronism with clock pulses 2 and 3, respectively, in a manner similar to the above. Thus, it is possible for a plurality of terminal devices to be successively controlled by a single main control unit, and even a plurality of patients can be subjected to hyperthermia treatments which are individually suitable to them at the same time and in parallel with each other. It is to be noted that this heating control by time-division multiplexing is employed in each of the embodiments (described hereinafter) in the same manner as the above.

The general operation of this embodiment will now be described. It is to be noted that, in the following description, a target value for the temperature of the body surface (referred to simply as the "surface temperature", hereinafter) which contacts the corresponding applicator 26 is set at 20° C., while a target value for the cancerous cell temperature is set at 43.5° C. The three patients in this embodiment are, respectively, referred to as the "patient No. 1", the "patient No. 2" and the "patient No. 3", hereinafter. It is further assumed that each of the variable impedance elements 38 is replaced by a variable impedance $Z_i$ (i=1, 2 or 3).

Figure 8:
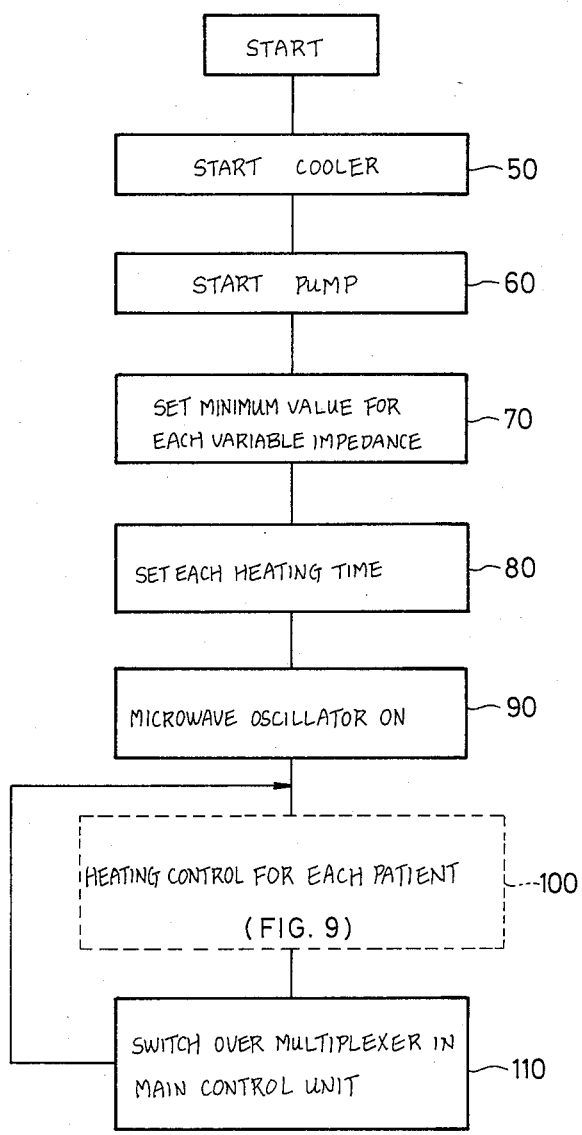
FIGS. 8 to 11 are flow charts which show the operation of the embodiment illustrated in FIG. 1.

First, the cooler 42 is started (Step 50 in FIG. 8), and after the water has been cooled down to 20° C., the pump 44 is started (Step 60 in FIG. 8). Then, the main control unit 28 sets a minimum value for each variable impedance $Z_i$ (that is, a maximum value for each microwave output) (Step 70 in FIG. 8). This setting is effected by combining a value (the difference between the respective power level values of incident and reflected waves) for the microwave output which is effectively supplied to each applicator 26 and which is obtained on the basis of the detected information delivered from the corresponding directional coupler 22 with a value (depth) which is set by the operator through the input/output unit 48 in accordance with the depth below the skin of the cancerous cells within the body of the patient concerned. It is assumed in this embodiment that maximum outputs of microwaves for the three patients which are set in Step 70 in FIG. 8 are respectively represented by $P_1$, $P_2$ and $P_3$. It is to be noted that the minimum attenuation rates may be previously set by employing a phantom model. After a minimum value for each variable impedance $Z_i$ has thus been set, the operator sets a heating time which is matched with the particular condition of each of the patients (Step 80 in FIG. 8).

Figure 9:
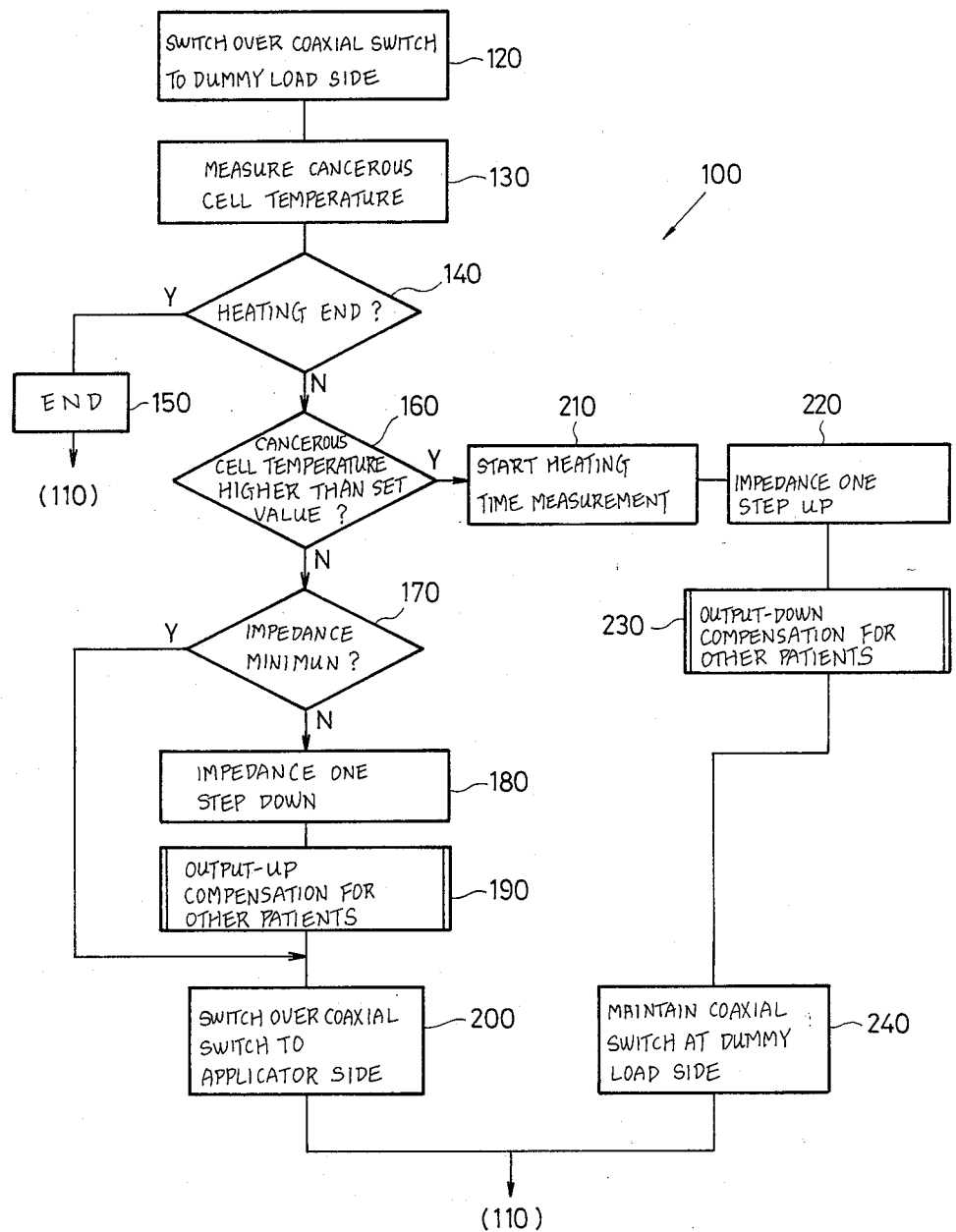

After these initial values have been set as described above, the microwave oscillator 12 is turned ON (Step 90 in FIG. 8), and the heating control shown in FIG. 9 is successively effected for each of the patients (Steps 100 and 110 in FIG. 8) by time-division multiplexing.

The flow chart of FIG. 9 will be described hereinunder in more detail. When the above-described clock pulse (e.g., 1) is input, the coaxial switch 18 for a first patient is switched over to the dummy load 16 (Step 120 in FIG. 9) in order to measure the cancerous cell temperature of this patient. This, after the microwave irradiation has been suspended so that the body 4 is not irradiated with microwaves, the cancerous cell temperature is measured (Step 130 in FIG. 9). The reason why no microwave irradiation is carried out during the measurement of cancerous cell temperature is that if microwave irradiation is continued, the cancerous cell temperature sensor 40 inserted into the body 4 of the patient would be affected by the microwaves, which fact would lead to errors in measurement of the cancerous cell temperature. After the cancerous cell temperature has been measured, a judgement is made (Step 140 in FIG. 9) as to whether or not the heating time has reached the value previously set (see Step 80 in FIG. 8). If YES, the treatment for the first patient alone is ended, and the process shifts to steps for treating another patient (Step 150 in FIG. 9; Step 110 in FIG. 8). More specifically, the multiplexers in the main control unit 28 are switched over, and input/output ports (not shown) of the main control unit 28 are changed over to the cancerous cell temperature sensor 40 and the coaxial switch 18 for the second patient (Step 110 in FIG. 8), thus executing processing for the second patient in a manner similar to the above.

If the judgement (Step 140 in FIG. 9) indicates that the heating time has not yet reached the set value, a judgement is made (Step 160 in FIG. 9) as to whether or not the cancerous cell temperature measured beforehand is higher than the set value (43.5° C.) which has previously been input by the operator. When the cancerous cell temperature is lower than the set value, the main control unit 28 steps down the variable impedance $Z_i$ for the patient concerned by one degree, thereby increasing the output setting value for the electromagnetic energy which is to be supplied to the body of the patient concerned. However, in this case it is necessary for the variable impedance $Z_i$ thus stepped down to be above the initially set minimum impedance (Steps 170 and 180 in FIG. 9). Then, the main control unit 28 effects a compensating adjustment (described later in detail) such as to step up the microwave outputs for the other patients (Step 190 in FIG. 9) and gives instructions to the coaxial switch 18 concerned whereby it is switched over to the corresponding applicator 26 (Step 200 in FIG. 9) (while the microwave oscillator 12 is kept ON), and heating for hyperthermia is continued on the basis of a newly set impedance value until a subsequent clock pulse 1 occurs. More specifically, the microwave irradiation and measurement of cancerous cell temperature are repeated in synchronism with clock pulses 1 until the cancerous cell temperature becomes higher than the set value. The value for the variable impedance $Z_i$ is stepped down by one degree every time the cancerous cell temperature is measured, and a subsequent microwave irradiation is effected with a newly set value.

On the other hand, when the judgement (Step 160 in FIG. 9) indicates that the cancerous cell temperature becomes higher than the set value as a result of the above-described microwave irradiation, measurement of the heating time is immediately started by the main control unit 28 (Step 210 in FIG. 9). At this time, since the cancerous cell temperature is slightly higher than the set value, the value for the variable impedance $Z_i$ is stepped up by one degree (Step 220 in FIG. 9) for the purpose of lowering the cancerous cell temperature, whereby the output setting value for the electromagnetic energy is lowered. Then, the main control unit 28 effects compensating adjustment (described later in detail) such as to step down the microwave outputs for the other patients (Step 230 in FIG. 9), and the switching of the coaxial switch 18 to the dummy load 16 is maintained as it is (Step 240 in FIG. 9), so that no microwave irradiation is effected. If the cancerous cell temperature is lower than the set value when a subsequent clock pulse 1 occurs, microwave irradiation is effected again through the above-described steps 170, 180, 190 and 200. This repetition of the heating control is effected within a very short period of time by the above-described time-division multiplexing.

The following is an explanation of the necessity of executing the above-described Steps 190 and 230.

Namely, during the repetition of the above-described heating control, as the variable impedance $Z_i$ (i=1, 2 or 3) is changed by one step (Steps 180 and 220 in FIG. 9), the reflection coefficient $r_i$ (i=1,2 or 3) corresponding thereto is also changed. In consequence, when the patient No. 1, for example, is being subjected to heating for hyperthermia, if the microwave output is adjusted by varying the variable impedance $Z_i$ in order to change the corresponding reflection coefficient $r_i$, the microwave outputs respectively applied to the patients Nos. 2 and 3 who are being simultaneously subjected to hyperthermia treatment are undesirably changed from the relationship which is expressed by the above-described formula (1), so that the control is disordered (this is, however, not applied to the case where the patient No. 3 is being subjected to the microwave output adjustment).

In order to prevent such disorder of control, in this embodiment a means is employed wherein, when the reflection coefficient in relation to a certain patient is changed, the reflection coefficients for the other patients which are affected by this change are compensated for such that changes in microwave outputs respectively supplied to these patients are cancelled. This compensating operation is conducted by the main control unit 28 in the above-described Steps 190 and 230 (see FIG. 9). The control effected in accordance with subroutines which are respectively executed in Steps 190 and 230 in FIG. 9 will be described later in detail (with reference to FIGS. 10 and 11) after the description of the overall control.

Incidentally, the main control unit 28 is programmed such that, when repeating the heating control shown in FIG. 9, the main control unit 28 actually executes only those steps which need to be executed for each repetition of the heating control. For example, a program is arranged such that, if Step 210 in FIG. 9 "Start Heating Time measurement" is once executed, this Step 210 is skipped in the control effected thereafter. In addition, when treatment for all the patients has been completed, a display lamp (not shown) is turned on, and the drive of the apparatus is suspended by the operator.

Figure 12:
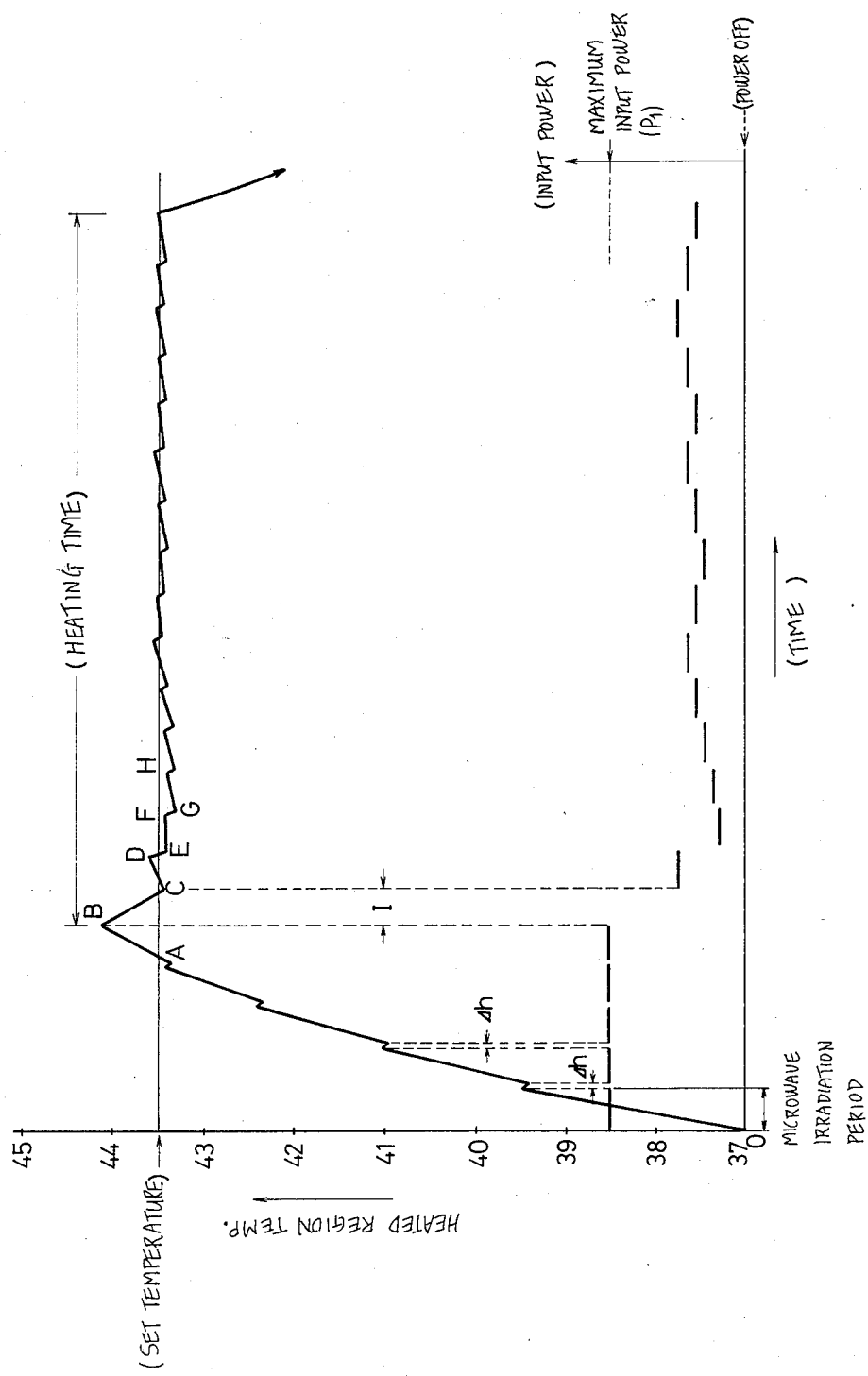
FIGS. 12 and 13 are graphs which show the action and operation of the embodiment illustrated in FIG. 1.

FIG. 12 shows a curve A representing changes with time in the cancerous cell temperature of a single patient measured during each microwave irradiation period, each non-irradiation period and each cancerous cell temperature measuring period (during which the heating control shown in FIG. 9 is processed), together with a broken line B representing changes in the microwave output.

Figure 7:
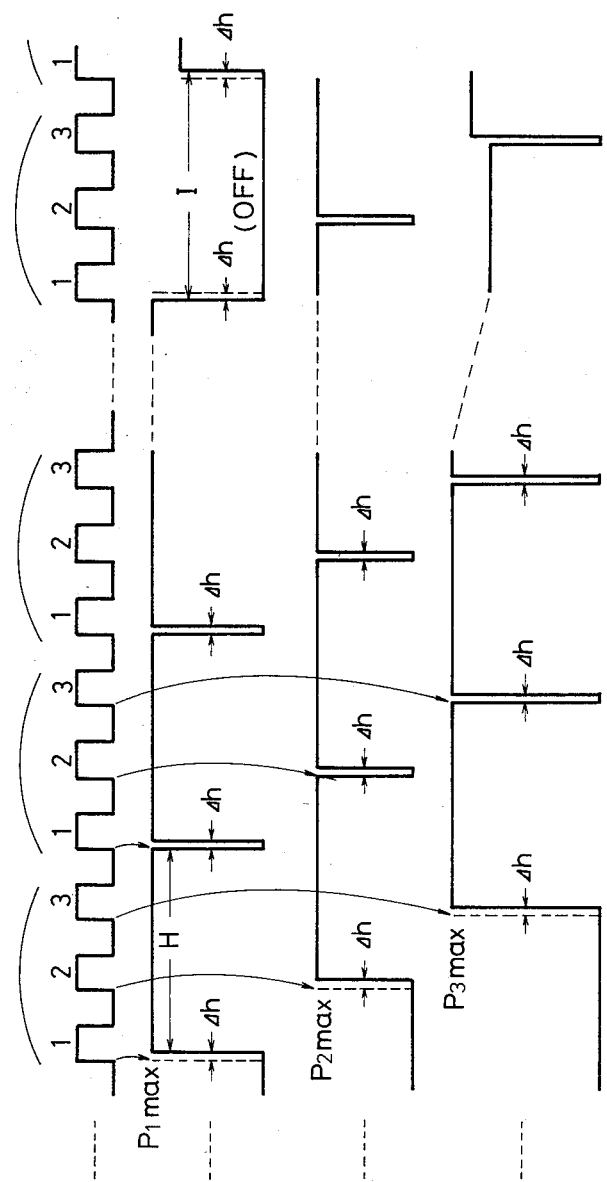
FIG. 7 is a timing chart which shows one example of the time-division multiplexing employed in the invention.

In FIG. 12, each of the intervals in which the cancerous cell temperature curve ascends corresponds to a microwave irradiation period, while each of the intervals $\Delta h$ in which the temperature curve descends corresponds to a period during which a cancerous cell temperature measuring operation is effected in synchronism with one clock pulse, as shown in FIG. 7. During each of the cancerous cell temperature measuring periods, the microwave output to the applicator 26 is zero (see Step 120 in FIG. 19).

The point B in FIG. 12 represents a point of time at which the cancerous cell temperature first exceeds the set temperature as the result of the microwave irradiation with a maximum output ($P_1$) on the basis of a minimum value (matched with each patient) for the variable impedance $Z_i$ and the measurement of the heating time is hence started. The above-described heating time is counted from this point B. Thereafter, instructions are continuously given to the effect that no microwave irradiation is to be performed until the cancerous cell temperature reaches 43.5° C. or below (see Step 240 in FIG. 9). During this period (the period between B and C in FIG., 12), the microwave output which is to be subsequently applied is newly set, and at the point of time when the cancerous cell temperature reaches 43.5° C. or below, microwave irradiation is resumed (during the period between C and D in FIG. 12). The time I between B and C corresponds to the time I, for example, which is shown in FIG. 7. During the period between C and D in FIG. 12, the cancerous cell temperature curve is less in terms of the degree of slope than that between A and B since the microwave output setting value has been lowered. In the case where the cancerous cell temperature does not reach 43.5° C. in the next microwave irradiation (e.g., during the period between E and F in FIG. 12) since the microwave output setting value has been excessively lowered during a cancerous cell temperature measuring period, the microwave output is stepped up during the next cancerous cell temperature measuring period (e.g., the period between F and G in FIG. 12) as shown in Step 180 in FIG. 9. In consequence, the degree of slope of the cancerous cell temperature curve is increased again (e.g., the period between G and H in FIG. 12). By virtue of such repetition of control, it is possible to obtain a heating control which involves substantially no ripple in heating for each of the patients.

Figure 13:
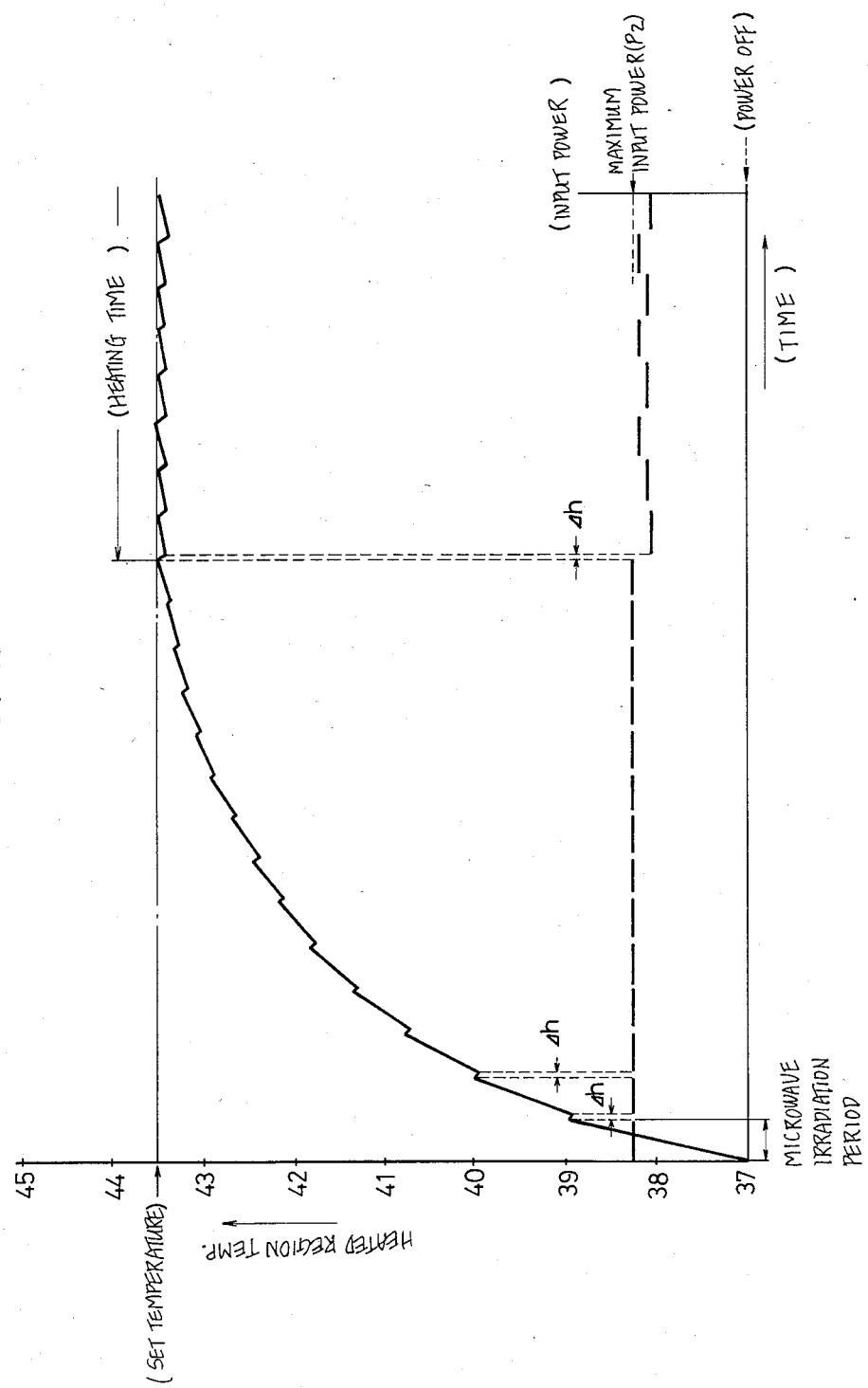

On the other hand, FIG. 13 shows changes in the cancerous cell temperature with time in the case where a minimum value for the variable impedance $Z_i$ is set at a relatively high level, that is, the maximum microwave output is set at a relatively low value ($P_2$) since targeted cancerous cells are present in a relatively deep part of the body of the patient. With respect to a patient who has a cancerous condition of this sort, hyperthermia treatment is effected in synchronism with, for example, a clock pulse 2 shown in FIG. 7.

The details (subroutines) of the microwave output compensating adjustment, that is, the reflection coefficient compensation shown in the above-described steps 190 and 230 in FIG. 9 will now be described with reference to FIGS. 10 and 11.

Figure 10:
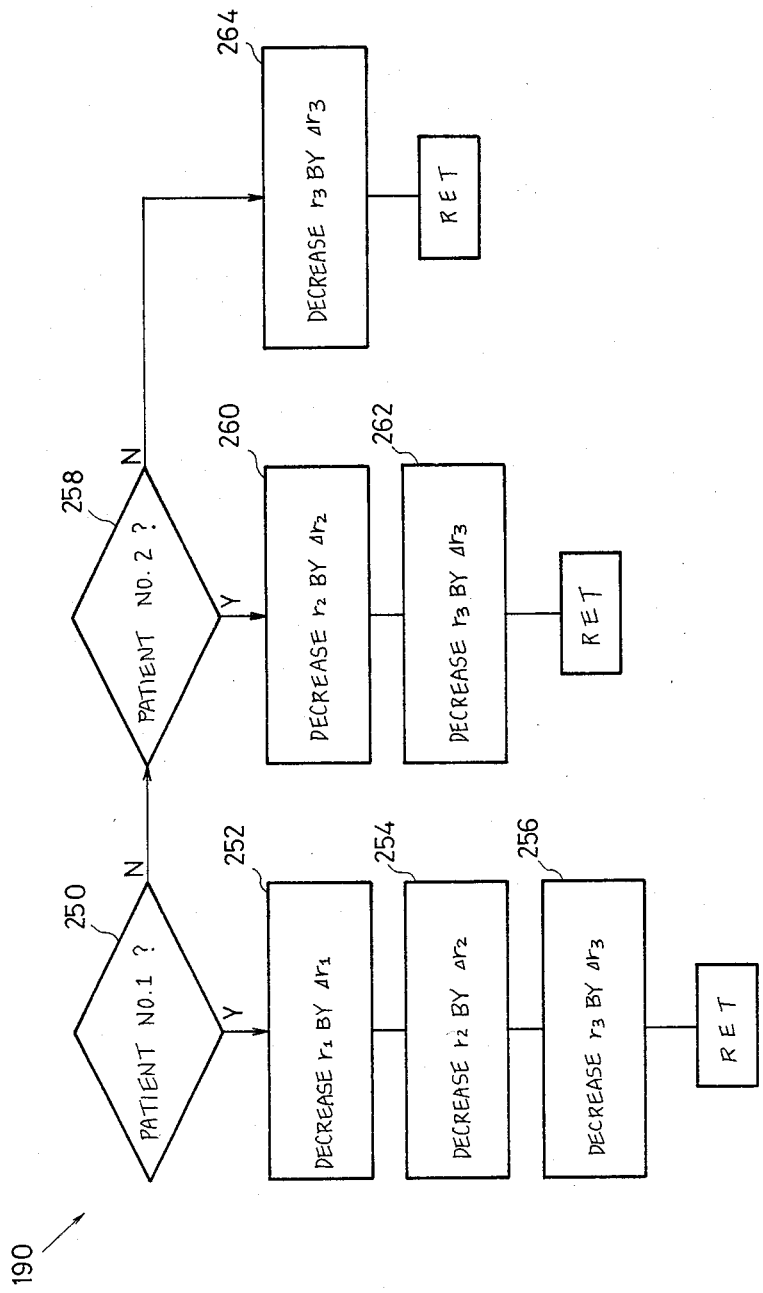

FIG. 10 shows a subroutine which is executed when the cancerous cell temperature is judged to be lower than the set value and in which the variable impedance $Z_i$ corresponding to the patient concerned is stepped down by one degree, thereby decreasing the reflection coefficient $r_i$ and hence increasing the microwave output (Step 190 in FIG. 9).

When the impedance $Z_i$ for the patient No. 1, for example, is stepped down by one degree (Step 250 in FIG. 10), if the reflection coefficient $r_1$ is decreased by $\Delta r_1$ (Step 252 in FIG. 10), it is possible to increase the microwave output for the patient No. 1 by the amount represented by the following formula:

$$\{1-(r_1-\Delta r_1)\}^2 P_0 - (1-r_1)^2 \cdot P_0 = 2 \cdot \Delta r_1 \cdot (1-r_1) \cdot P_0$$

In such a case, it is necessary with respect to the other patients Nos. 2 and 3 to decrease the reflection coefficients $r_2$ and $r_3$ and by $\Delta r_2$ and $\Delta r_3$, respectively (Steps 254 and 256 in FIG. 10) in order to maintain the microwave outputs for the patients Nos. 2 and 3 at constant levels, respectively. In this case, $\Delta r_2$ is calculated from the following formula:

$$(1-r_2)^2 \cdot r_1^2 \cdot P_0 = \{(1-(r_2-\Delta r_2)\}^2$$
$$(r_1 - \Delta r_1)^2 \cdot P_0$$

On the other hand, $\Delta r_3$ is calculated as follows:

$$(1-r_3)^2 \cdot r_1^2 \cdot r_2^2 \cdot P_0 = \{(1-(r_3-\Delta r_3)\}^2$$
$$(r_1 - \Delta r_1)^2 \cdot (r_2 - \Delta r_2)^2 \cdot P_0$$

When the impedance $Z_2$ for the patient No. 2 is stepped down by one degree (Step 258 in FIG. 10), if the reflection coefficient $r_2$ is decreased by $\Delta r_2$ (Step 260 in FIG. 10), it is possible to increase the microwave output for the patient No. 2 by the amount given by the following formula:

$$\{(1-(r_2-\Delta r_2)\}^2 \cdot r_1^2 \cdot P_0 - (1-r_2)^2 \cdot r_1^2 \cdot P_0 =$$
$$2 \cdot \Delta r_2 \cdot (1-r_2) \cdot r_1^2 \cdot P_0$$

In such a case, it is necessary for the reflection coefficient $r_3$ to be decreased by $\Delta r_3$ (Step 262 in FIG. 10) in order to maintain the microwave output for the patient No. 3 at a constant level (there is, in this case, no effect on the microwave output applied to the patient No. 1). In this case, $\Delta r_3$ is obtained from the following formula:

$$(1-r_3)^2 \cdot r_1^2 \cdot r_2^2 \cdot P_0 = \{1-(r_3-\Delta r_3)\}^2 \cdot r_1^2 \cdot (r_2-\Delta r_2)^2 \cdot P_0$$

On the other hand, when the impedance $Z_3$ for the patient No. 3 is stepped down by one degree, if the reflection coefficient $r_3$ is decreased by $\Delta r_3$ (Step 264 in FIG. 10), it is possible to increase the microwave output for the patient No. 3 by the amount represented by the following formula:

$$\{1-(r_3-\Delta r_3)\}^2 \cdot r_1^2 \cdot r_2^2 \cdot P_0 - (1-r_3)^2 \cdot r_1^2 \cdot r_2^2 \cdot P_0 =$$

-continued
$$2 \cdot \Delta r_3 \cdot (1 - r_3) \cdot r_1^2 \cdot r_2^2 \cdot P_0$$

In this case, it is not necessary to take into consideration any effect on the microwave outputs respectively applied to the other patients Nos. 1 and 2.

Figure 11:
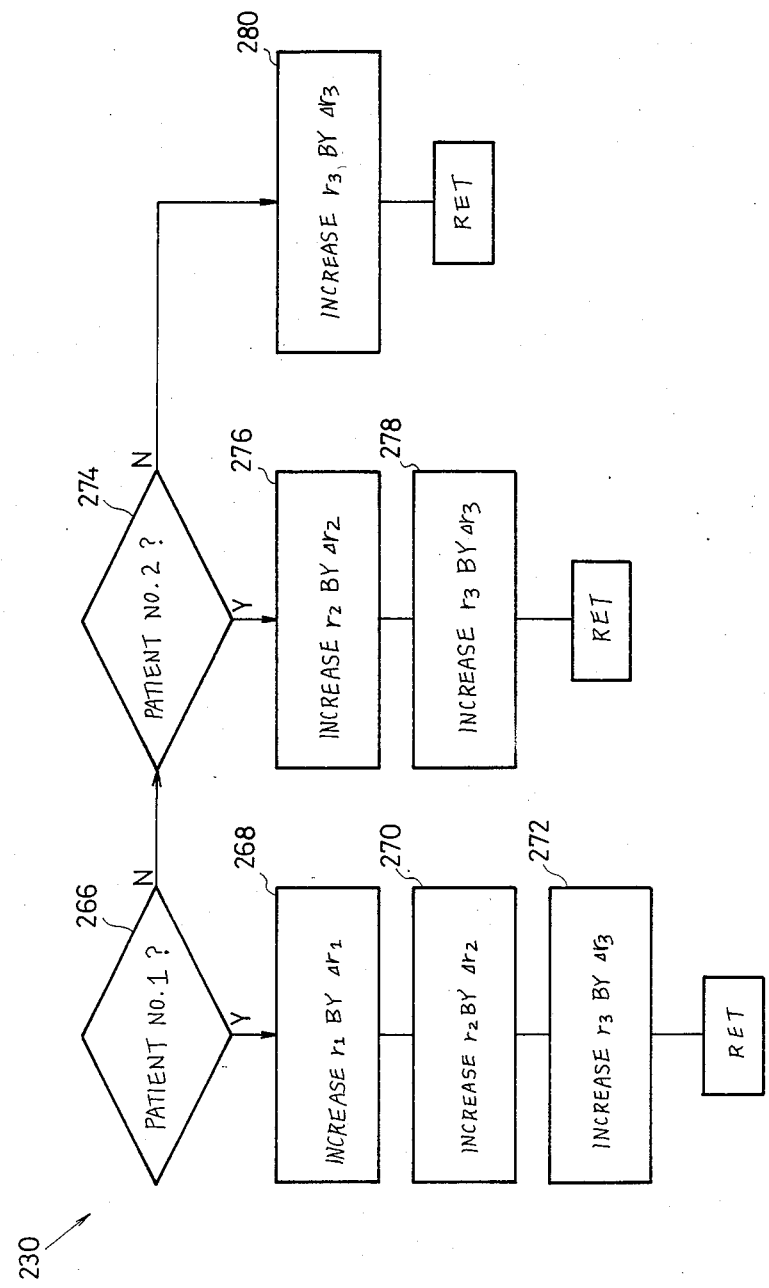

The following is a description of the subroutine which is executed in the case where the variable impedance $Z_i$ is stepped up by one degree (Step 230 in FIG. 9) with reference to FIG. 11.

For example, when the impedance $Z_i$ for the patient No. 1 is stepped up by one degree (Step 266 in FIG. 11), if the reflection coefficient $r_1$ is increased by $\Delta r_1$ (Step 268 in FIG. 11), it is possible to decrease the microwave output for the patient No. 1 by the amount represented by the following formula:

$$(1 - r_1)^2 \cdot P_0 - \{1 - (r_1 + \Delta r_1)\}^2 \cdot P_0 = 2 \cdot \Delta r_1 \cdot (1 - r_1) P_0$$

In such a case, it is necessary with respect to the other patients Nos. 2 and 3 to increase the reflection coefficients $r_2$ and $r_3$ by $\Delta r_2$ and $\Delta r_3$, respectively, in order to maintain the microwave outputs for the patients Nos. 2 and 3 at constant levels, respectively (Steps 270 and 272 in FIG. 11). In this case, $\Delta r_2$ is calculated from the following formula:

$$(1 - r_2)^2 \cdot r_1^2 \cdot P_0 = \{1 - (r_2 + \Delta r_2)\}^2 \cdot (r_1 + \Delta r_1)^2 \cdot P_0$$

On the other hand, $\Delta r_3$ is calculated from the following formula:

$$(1 - r_3)^2 \cdot r_1^2 \cdot r_2^2 \cdot P_0 =$$

$$\{1 - (r_3 + \Delta r_3)\}^2 \cdot (r_1 + \Delta r_1)^2 \cdot (r_2 + \Delta r_2)^2 \cdot P_0$$

When the impedance $Z_2$ for the patient No. 2 is stepped up by one degree (Step 274 in FIG. 11), if the reflection coefficient $r_2$ is increased by $\Delta r_2$ (Step 276 in FIG. 11), it is possible to decrease the microwave output for the patient No. 2 by the amount represented by the following formula:

$$(1 - r_2)^2 \cdot r_1^2 \cdot P_0 - \{1 - (r_2 + \Delta r_2)\}^2 \cdot r_1^2 \cdot P_0 =$$

$$2 \cdot \Delta r_2 \cdot (1 - r_2) \cdot r_1^2 \cdot P_0$$

In this case, it is necessary to increase the reflection coefficient $r_3$ for the other patient No. 3 (there is, in this case, no effect on the microwave output applied to the patient No. 1) by $\Delta r_3$ in order to maintain the microwave output applied thereto at a constant level (Step 278 in FIG. 11). In this case, $\Delta r_3$ is obtained from the following formula:

$$(1 - r_3)^2 \cdot r_1^2 \cdot r_2^2 \cdot P_0 = \{1 - (r_3 + \Delta r_3)\}^2 \cdot r_1^2 \cdot (r_2 + \Delta r_2)^2 \cdot P_0$$

On the other hand, when the impedance $Z_3$ for the patient No. 3 is stepped up by one degree, if the reflection coefficient $r_3$ is increased by $\Delta r_3$ (Step 280 in FIG. 11), it is possible to decrease the microwave output for the patient No. 3 by the amount represented by the following formula:

$$(1 - r_3)^2 \cdot r_1^2 \cdot r_2^2 \cdot P_0 - \{1 - (r_3 + \Delta r_3)\}^2 \cdot r_1^2 \cdot r_2^2 \cdot P_0 =$$

-continued
$$2 \cdot \Delta r_3 \cdot (1 - r_3) \cdot r_1^2 \cdot r_2^2 \cdot P_0$$

In this case, it is not necessary to take into consideration any effect on the microwave outputs respectively supplied to the other patients Nos. 1 and 2.

As has been described above, it is possible according to the first embodiment to effect a highly accurate control such that the cancerous cell temperature is maintained at a set value or at values in close proximity thereto over a long period of time, and it is possible for even a plurality of patients to be subjected to hyperthermia treatment at the same time and in parallel with each other, which fact advantageously leads to a further increase in treatment efficiency. Since in this case a single microwave source (microwave oscillator) and a single main control unit are conveniently used in common to control the various terminal devices, it is favorably possible to reduce the size of the apparatus as a whole, improve its transportability and controllability and hence lessen the load imposed on the operator in contrast to a hyperthermia apparatus which is equipped with a plurality of electromagnetic wave generating means. Further, in this embodiment the electromagnetic wave generating means is continuously kept operative and, while doing so, microwaves generated thereby are effectively ON/OFF controlled by the electromagnetic wave switching means, which fact advantageously facilitates the control operation. Since electromagnetic waves are branched off by the operation of the variable electromagnetic waves are branched off by the operation of the variable electromagnetic waves are branching means and that of the main control unit and since the respective output levels of the branched electromagnetic waves are variably controlled, there is no need to add any constituent element for the output level adjustment, so that it is possible to reduce the size of the apparatus, simplify the arrangement thereof and stabilize the control operation. Moreover, when a plurality of patients are simultaneously subjected to hyperthermia treatment, control is effectively executed for each individual patient. It is therefore advantageously possible for various patients to be individually subjected to treatments in parallel with each other which are individually suitable to them even when the conditions of these patients differ from one another by properly setting respective heating times.

Second Embodiment:

A second embodiment of the invention will now be described with reference to FIGS. 14 and 15, in which the same constituent elements as those in the first embodiment are denoted by the same reference numerals (the same is the case with each of the embodiments described hereinafter).

Figure 14:
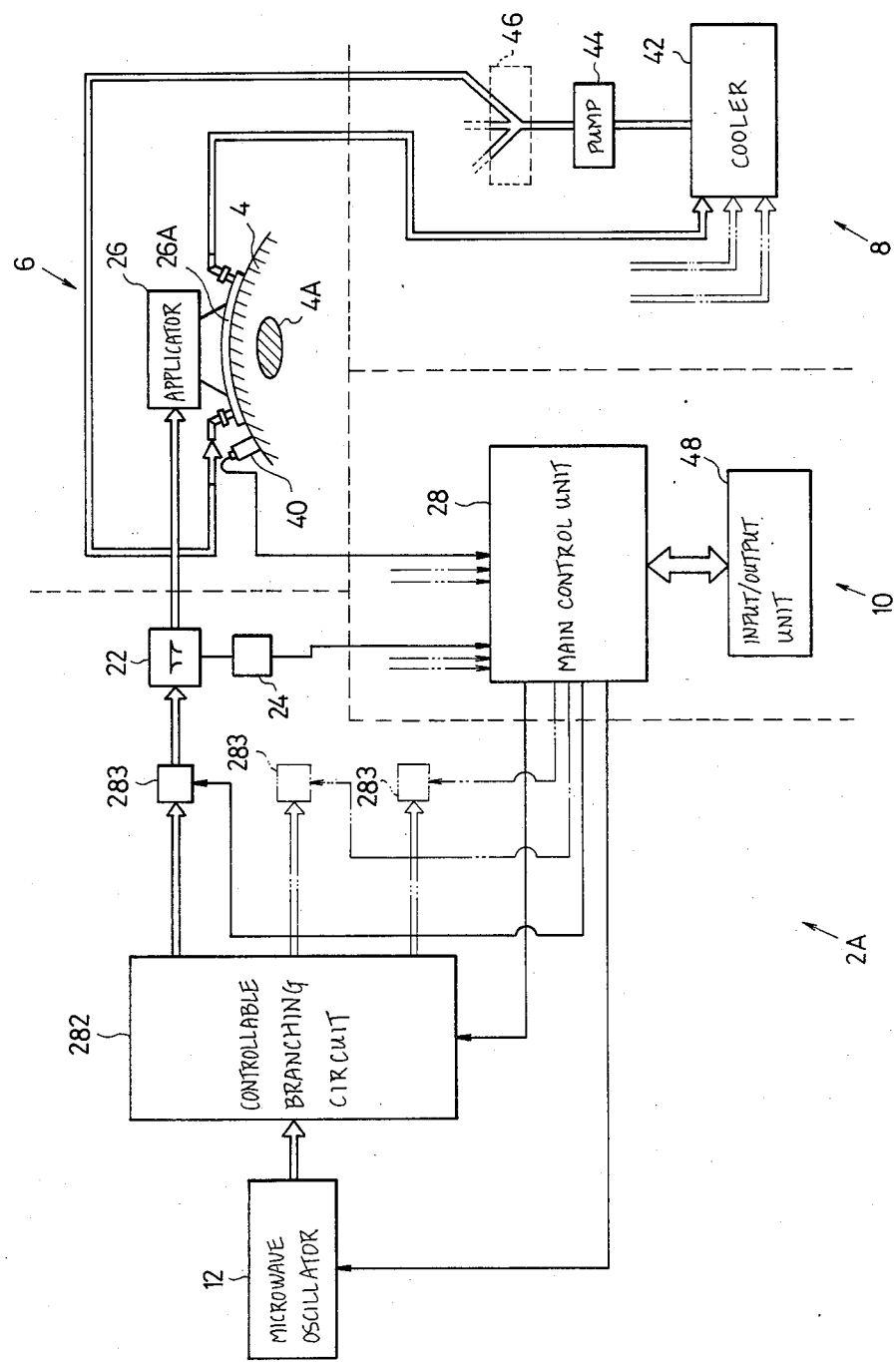
FIG. 14 is a general system diagram of a second embodiment of the invention.

The second embodiment is generally arranged such as that shown in FIG. 14 on the basis of the gist which is similar to that of the above-described first embodiment. The second embodiment particularly differs from the first embodiment in the arrangement of a controllable branching circuit 282 serving as a variable electromagnetic wave branching means and that of each of the coaxial switches 283 in its electromagnetic wave supply section 2A.

Figure 15:
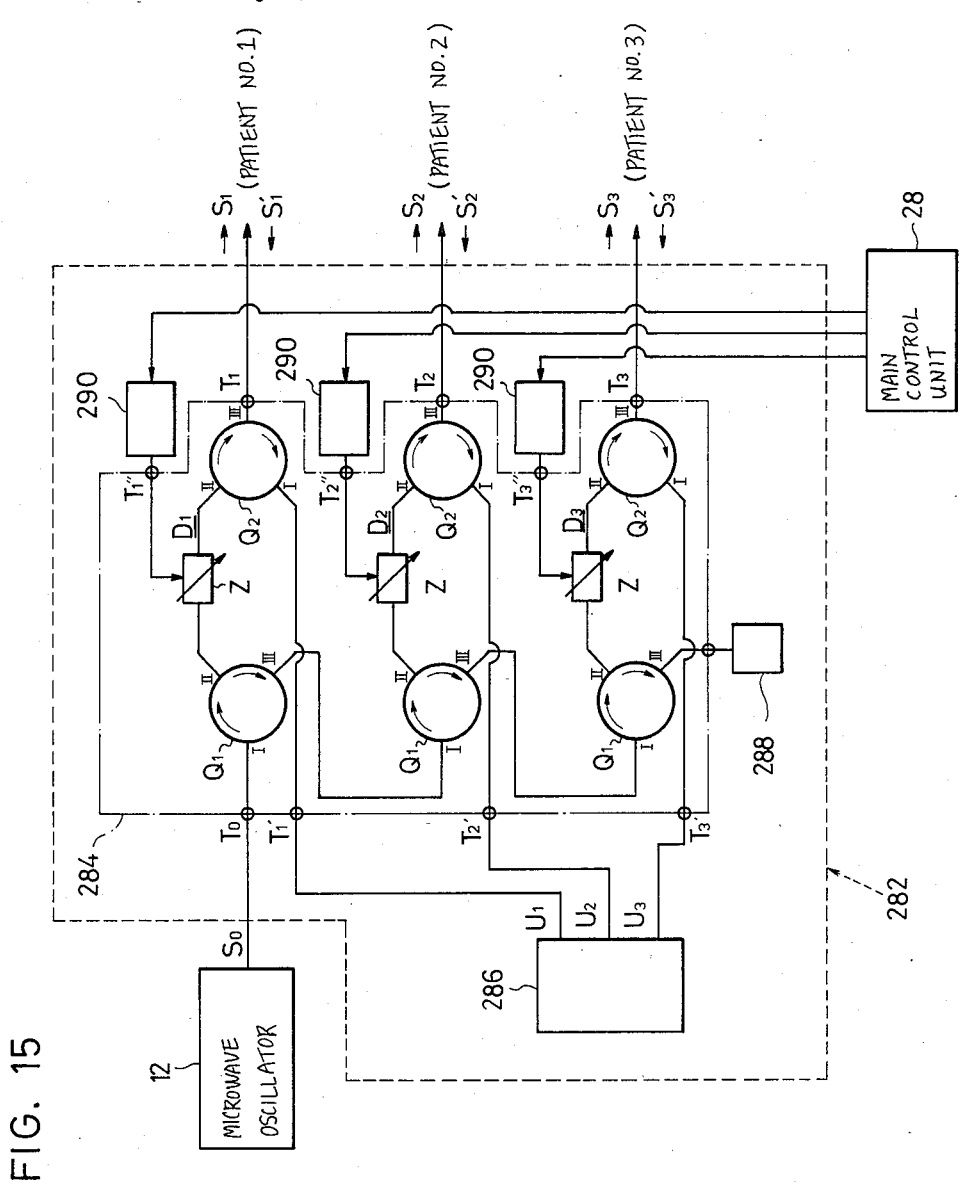
FIG. 15 is a block diagram which schematically shows the arrangement of a controllable branching circuit in the embodiment illustrated in FIG. 14.

Referring to FIG. 15 which shows the arrangement of the controllable branching circuit 282, this circuit 282 is composed of a distributor 284, dummy loads 286, 288 and variable voltage sources 290.

The distributor 284 has i (i=1,2, or 3; the same is the case with representations in the following description) number of distributing circuits $D_i$, each of which includes branching-type circulators $Q_1$ and $Q_2$ each having first, second and third ports I, II and III. Since the circulators $Q_1$ and $Q_2$ are per se known, detailed description thereof is omitted. In each of the circulators $Q_1$ and $Q_2$, the first and second ports I and II pair with each other in such a relation that microwaves supplied from the first port I are obtained from the second port II. The second and third ports II and III and the third and first ports III and I respectively pair with each other in a manner similar to the above. Thus, the distributing circuits $D_i$ have their respective variable impedance circuits Z interconnected with each other, each variable impedance circuit Z being arranged such that it is possible for the second port II of each of the circulators $Q_1$ and $Q_2$ to vary the impedance by virtue of the voltage control of the corresponding variable voltage source 290. Accordingly, the third port III of the circulator $Q_1$ in the distributing circuit $D_1$ is connected to the first port I of the circulator $Q_1$ in the distributing circuit D (i+1). However, the third port III of the circulator $Q_1$ in the distributing circuit $D_3$ which constitutes the final stage is connected to the dummy load 288. The first port I of the circulator $Q_1$ in the distributing circuit $D_1$ is connected to the microwave oscillator 12 through an input terminal $T_0$ of the distributor 284. Further, the third port III of the circulator $Q_2$ in the distributing circuit $D_i$ is connected to the corresponding applicator through an input/output terminal $T_i$ of the distributor 284, while the first port I of the circulator $Q_2$ of the distributing circuit $D_i$ is connected to an input terminal $U_i$ of the dummy load 286 through an output terminal $T_i'$ of the distributor 284. Accordingly, when the distributing circuit $D_i$ has a microwave of power $P_i$ supplied to the first port I of its circulator $Q_1$, the microwave is transmitted to the second port II. However, this microwave is partially reflected at the position of the variable impedance circuit Z back to the second port II. The power of this reflected wave is given by $r_i^2 P_i$, where $r_i$ represents a reflection coefficient at the position of the variable impedance circuit Z. Accordingly, the microwave of power $P_i$ supplied to the first port I of the circulator $Q_1$ is divided into two microwaves, one of them having a power represented by $(1-r_i)^2 P_i$ and the other having a power represented by $r_i^2 P_i$. The former divided microwave is transmitted to the input/output terminal $T_i$ through the variable impedance circuit Z and the second and third ports II and III of the circulator $Q_2$, while the latter divided microwave is transmitted to the first port I of the circulator $Q_1$ in the distributing circuit D (i+1) through the second and the third ports II and III of the circulator $Q_1$.

Accordingly, if a microwave having a power $P_0$ is supplied to the input terminal $T_0$ of the distributor 284, the first ports I of the distributing circuits $D_1$, $D_2$ and $D_3$ are respectively supplied with microwaves having respective powers represented by $P_0$, $r_1^2 \cdot P_0$ and $r_1^2 \cdot r_2^2 \cdot P_0$.

In consequence, it is possible to obtain at the input/output terminals $T_1$, $T_2$ and $T_3$ microwaves having powers respectively represented by $(1-r_1)^2 \cdot P_0$, $(1-r_2)^2 \cdot r_1^2 \cdot P_0$ and $(1-r_3)^2 \cdot r_1^2 \cdot r_2^2 \cdot P_0$.

In other words, the controllable branching circuit 282 is arranged such that microwaves $S_1$, $S_2$ and $S_3$ are respectively supplied to the applicators 26 from the input/output terminals $T_1$, $T_2$ and $T_3$ and the energy of the microwaves $S_1'$, $S_2'$ and $S_3'$ which are respectively reflected from the applicators and the like is consumed by the dummy load 286.

In this case, the power ratio between the microwaves $S_1$, $S_2$ and $S_3$ which are obtained by dividing the power of the microwave $S_0$ by means of the distributor 284 is determined in accordance with the relationship between the reflection coefficients $r_1$, $r_2$ and $r_3$ in the distributing circuits $D_1$, $D_2$ and $D_3$, as will be clear from the above description. On the other hand, the reflection coefficient $r_i$ is determined in accordance with the impedance of the variable impedance circuit Z in the distributing circuit $D_i$. In consequence, it is possible to obtain microwaves $S_1$, $S_2$ and $S_3$ having a desired power ratio therebetween by adjusting the variable impedance circuit Z of each of the distributing circuits $D_1$, $D_2$ and $D_3$ from the main control unit 28.

Since the controllable branching circuit 282 is arranged and operates as described above, it is not necessary for the electromagnetic supply section 2A of the second embodiment to employ the dummy loads 16 and the isolators 20 which are required in the first embodiment, so that the arrangement of this embodiment is advantageously simplified. Further, the ON/OFF control of the switching operation of each of the coaxial switches 283 serving as electromagnetic wave switching means is effected in accordance with instructions delivered from the main control unit 28.

The arrangement of the other portions of this embodiment is the same as that of the first embodiment.

With the above arrangement, the operation of the second embodiment is substantially the same as that of the first embodiment (see FIGS. 7 to 13), except for the following:

(1) In the second embodiment, a minimum impedance for each variable impedance circuit Z is set in Step 70 in FIG. 8 (it is assumed that each variable impedance circuit Z is represented by a variable impedance $Z_i$ (i=1, 2 or 3)).

(2) In the second embodiment, the coaxial switch 283 is turned OFF in Step 120 in FIG. 9, whereby microwaves are fully reflected toward the controllable branching circuit 282 and the microwave output toward the applicator 26 is made zero. This is done because even if microwaves are fully reflected, the reflected waves are applied to the dummy load 286 in the controllable branching circuit 282 and, therefore, no undesirable reflection occurs.

(3) In the second embodiment, the coaxial switch 283 is turned ON in Step 200 in FIG. 9, while the coaxial switch 283 is maintained in the OFF state in Step 240 in FIG. 9, whereby the ON/OFF control of electromagnetic wave irradiation is effected.

Accordingly, it is possible according to the second embodiment to obtain advantageous effects which are substantially equivalent to those offered by the first embodiment. In addition, by virtue of the favorable operation of the controllable branching circuit 282 serving as a variable electromagnetic wave branching means, it becomes unnecessary to provide the dummy loads 16 connected to the electromagnetic wave switching means and the isolators 20 respectively provided for the electromagnetic wave paths which are required in the first embodiment. In consequence, simplification of the arrangement of the apparatus as a whole is intensified correspondingly.

Third Embodiment:

A third embodiment of the invention will now be described with reference to FIGS. 16 to 18.

This embodiment aims at facilitating and expediting the control of cancerous cell temperature by individually controlling the cooling of the surface of the body of each patient during hyperthermia treatment so that the surface temperature is properly adjusted, in addition to the object of the above-described first embodiment. To this end, the flow rate of cooling water in this embodiment is controlled.

Figure 16:
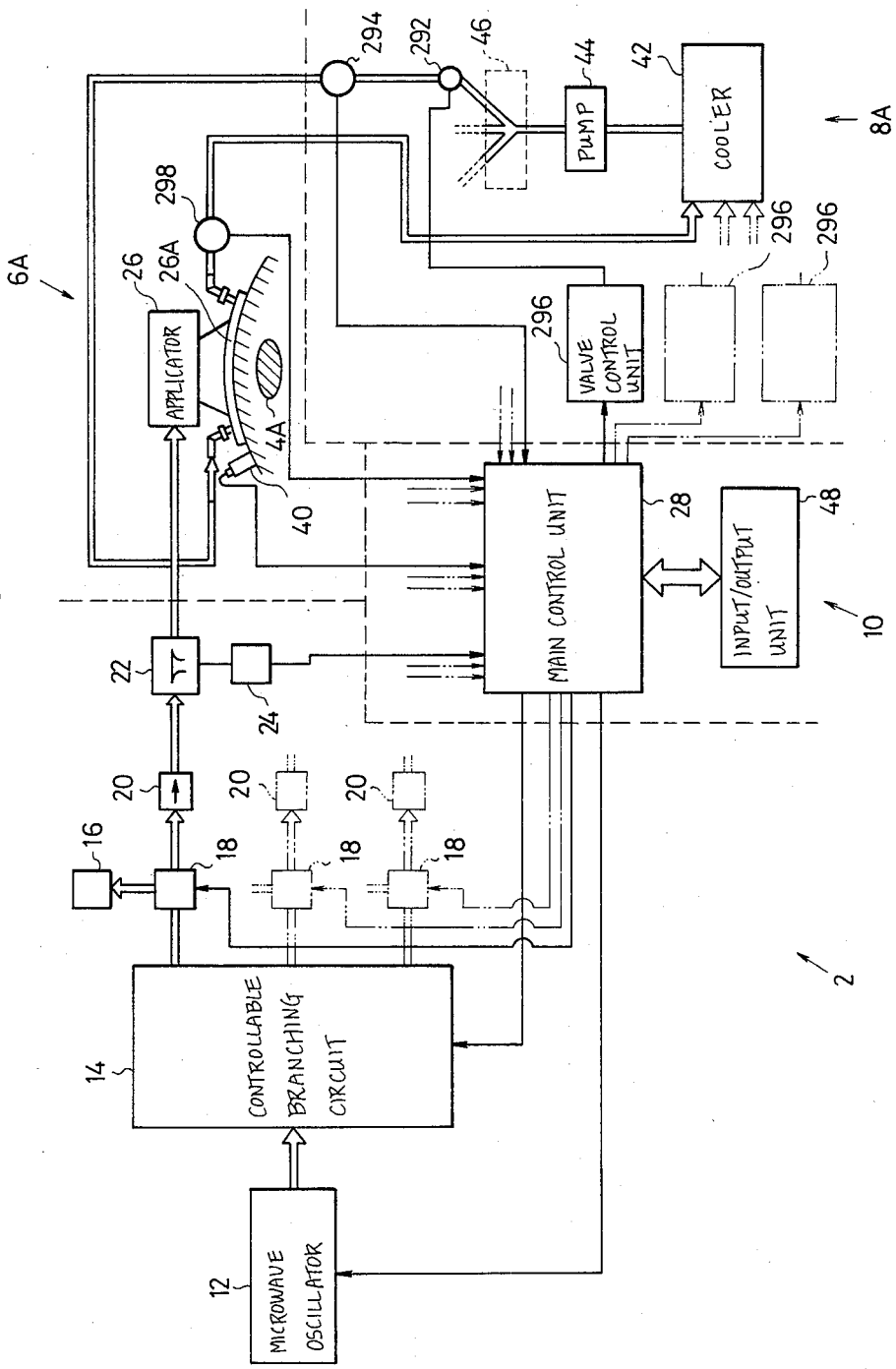
FIG. 16 is a general system diagram of a third embodiment of the invention.

Referring first to FIG. 16, in the cooling water supply section 8A of this embodiment, water is distributed to the cooling mechanisms 26A by the coolant distributor 46. The coolant distributor 46 is provided on its outlet side with flow rate adjusting valves 292 and flow rate sensors 294, which correspond to the respective coolant paths. The flow rate information detected by each of the flow rate sensors 294 is input to the main control unit 28 in the control section 10 and is subjected to a judgement by a predetermined control function of the main control unit 28. The main control unit 28 delivers control signals to valve control units 296 respectively provided for the valves 292 in accordance with need, thereby controlling the degree of opening of the corresponding valves 292. In consequence, the flow rate of cooling water is adjusted in accordance with the degree of opening of each valve 292, and the temperature of the body surface at the hyperthermia treatment region is thereby adjusted. This adjustment of the temperature of the body surface is an auxiliary means relative to the cancerous cell temperature control.

In the third embodiment, a coolant temperature sensor 298 serving as one of the heated region temperature detecting means is additionally provided on the outlet side of the cooling mechanism 26A of each applicator 26 in the electromagnetic wave irradiating section 6A (see FIG. 16). The coolant temperature information obtained by each of the coolant temperature sensors 298 is input to the main control unit 28 with respect to each treatment system and is employed as a reference value for various controls. The reason why the coolant temperature information is incorporated in the operation of controlling the surface temperature is that the temperature of cooling water is substantially equal to the surface temperature of the body of a patient in a stationary state and it is therefore possible for the surface temperature to be indirectly obtained from the degree of change in the temperature of the cooling water on the outlet side of each cooling mechanism 26A.

Inputting of flow rate information to the main control unit 28 and delivering of control signals from the main control unit 28 are effected for each of the treatment systems by switching over the multiplexers in a manner similar to that in the first embodiment.

The arrangement of the other portions of this embodiment is the same as that of the first embodiment.

The following is a description of the general operation of the third embodiment with reference to FIGS. 17 and 18, in which those steps which represent the same operations as the ones in the first embodiment are denoted by the same reference numerals (the same is the case with each of the embodiments described hereinafter). It is assumed that a target value for the cancerous cell temperature is set at 43.5° C., while a target value for the surface temperature is set at 20° C.

Figure 17:
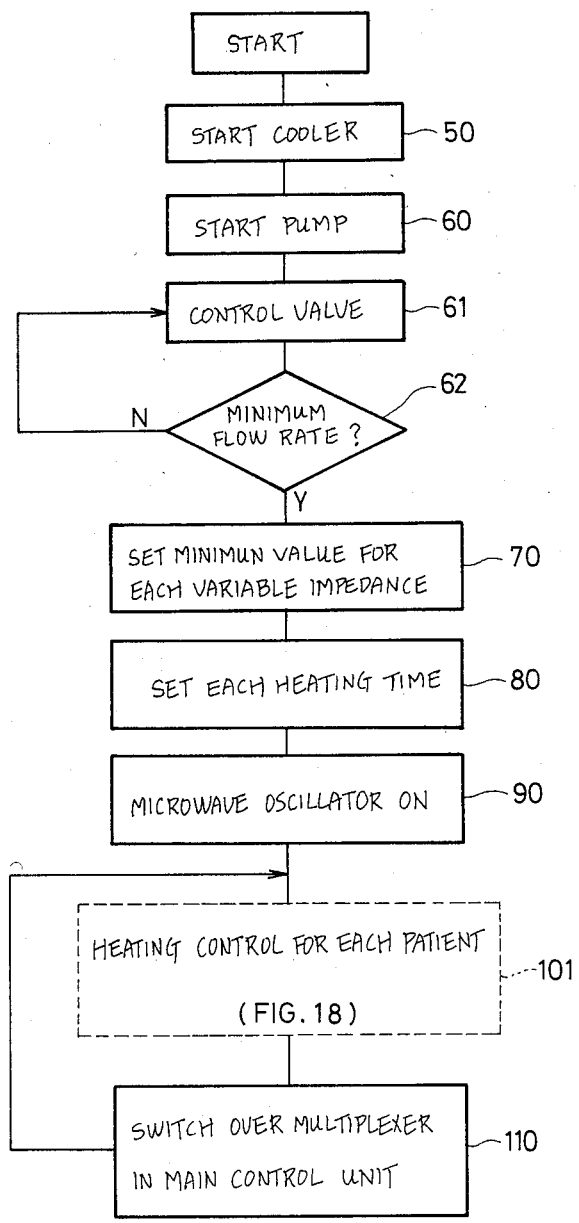
FIGS. 17 and 18 are flow charts which show the operation of the embodiment illustrated in FIG. 16.

First, the cooler 42 is started (Step 50 in FIG. 17), and the pump 44 is started (Step 60 in FIG. 17). Then, the degree of opening of each valve 292 is controlled by the main control unit 28 on the basis of the flow rate information obtained by the corresponding flow rate sensor 294 such that the amount of cooling water recirculating is minimized (Steps 61 and 62 in FIG. 17). Then, in a manner similar to that in each of the above-described embodiments, a minimum value for each of the variable impedances in the controllable branching circuit 14 is set (Step 70 in FIG. 17), a heating time for each patient is set (Step 80 in FIG. 17), and the microwave oscillator 12 is turned ON (Step 90 in FIG. 17). Thereafter, a heating control peculiar to each patient is individually effected by time-division multiplexing (see FIG. 7) until the treatment for all the patients is ended (Steps 101 and 110 in FIG. 17).

Figure 18:
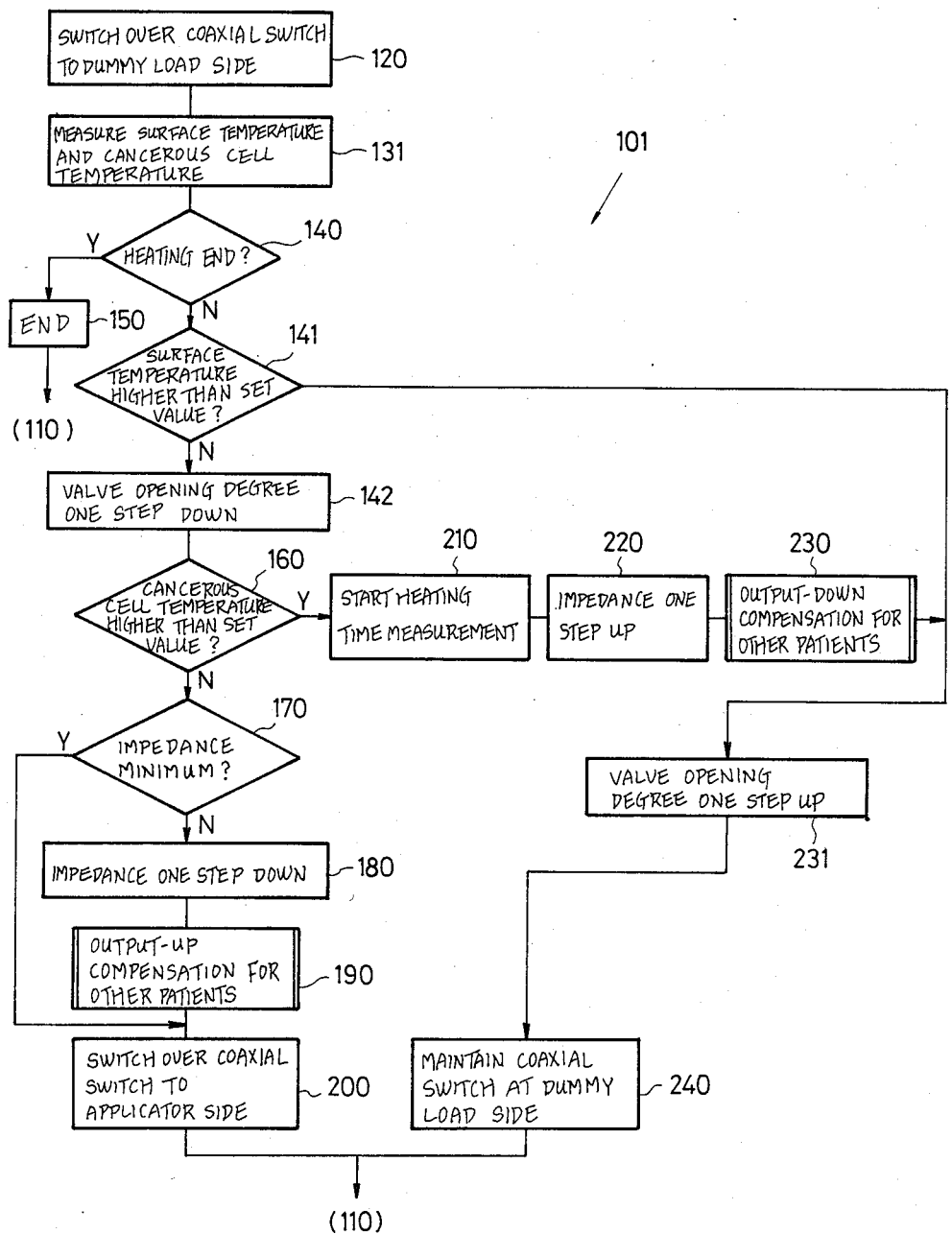

The heating control for each individual patient is effected in accordance with the flow chart shown in FIG. 18. According to this flow chart, the following functions are added to the control operation of the first embodiment which is shown in FIG. 9:

(1) The surface temperature is measured on the basis of not only the cancerous cell temperature but also the coolant temperature information obtained from the corresponding coolant temperature sensor 298 (Step 131 in FIG. 18).

(2) In accordance with the result of the judgement (Step 141 in FIG. 18) as to whether or not the surface temperature is higher than the set value, the corresponding valve 292 is closed (Step 142 in FIG. 18) or opened (Step 231 in FIG. 18) by one step.

The other operations of this embodiment are the same as those shown in FIG. 9 which illustrates the operation of the first embodiment. In the above-described function (2), when the surface temperature is lower than the set value, the valve 292 is closed by one step (Step 142 in FIG. 18). This is done because it is necessary to raise the surface temperature (however, in this case it is necessary for the flow rate of cooling water to be high enough to maintain a minimum amount of cooling water for recirculation in order to prevent the surface of the body of the patient from being thermally burned) and thereby to effect an auxiliary temperature adjustment also at the surface of the patient body so that the cancerous cell temperature being heated by the microwave irradiation quickly reaches the set value. The surface temperature is measured indirectly by sensor 298 which measures the temperature of the coolant (step 131 in FIG. 18) as it exits the cooling mechanism. In other words, the temperature of the exiting coolant is regarded as the surface temperature, because the temperature of such coolant is substantially the same as the surface temperature in steady state operation. On the other hand, the reason why the valve 292 is opened by one step (Step 231 in FIG. 18) when the surface temperature is higher than the set value is that it is necessary to lower the surface temperature and thereby to effect an auxiliary temperature adjustment also at the body surface so that the cancerous cell temperature quickly returns to the set value.

Since this embodiment operates in this manner, the heating characteristic curves thereof are similar to those of the first embodiment (see FIGS. 12 and 13).

Thus, it is possible according to the third embodiment to obtain advantageous effects which are substantially equivalent to those which are offered by the first embodiment. In addition, it is advantageously possible for the control of heating the cancerous cells within the body to be even more smoothly and precisely effected by auxiliarily controlling the surface temperature of the body. Since in this embodiment the surface temperature, in addition to the internal temperature of the body, is employed as a reference value for effecting a feedback control, it is possible for the surface temperature at the heated region to be more accurately and stably maintained at a predetermined value (e.g., 20° C.) at which the patient suffers no pain. Thus, it is advantageously possible to prevent the occurrence of any thermal burn or the like which would otherwise be caused by a rise in temperature as the result, for example, of a sudden change in the blood flow.

Figure 19:
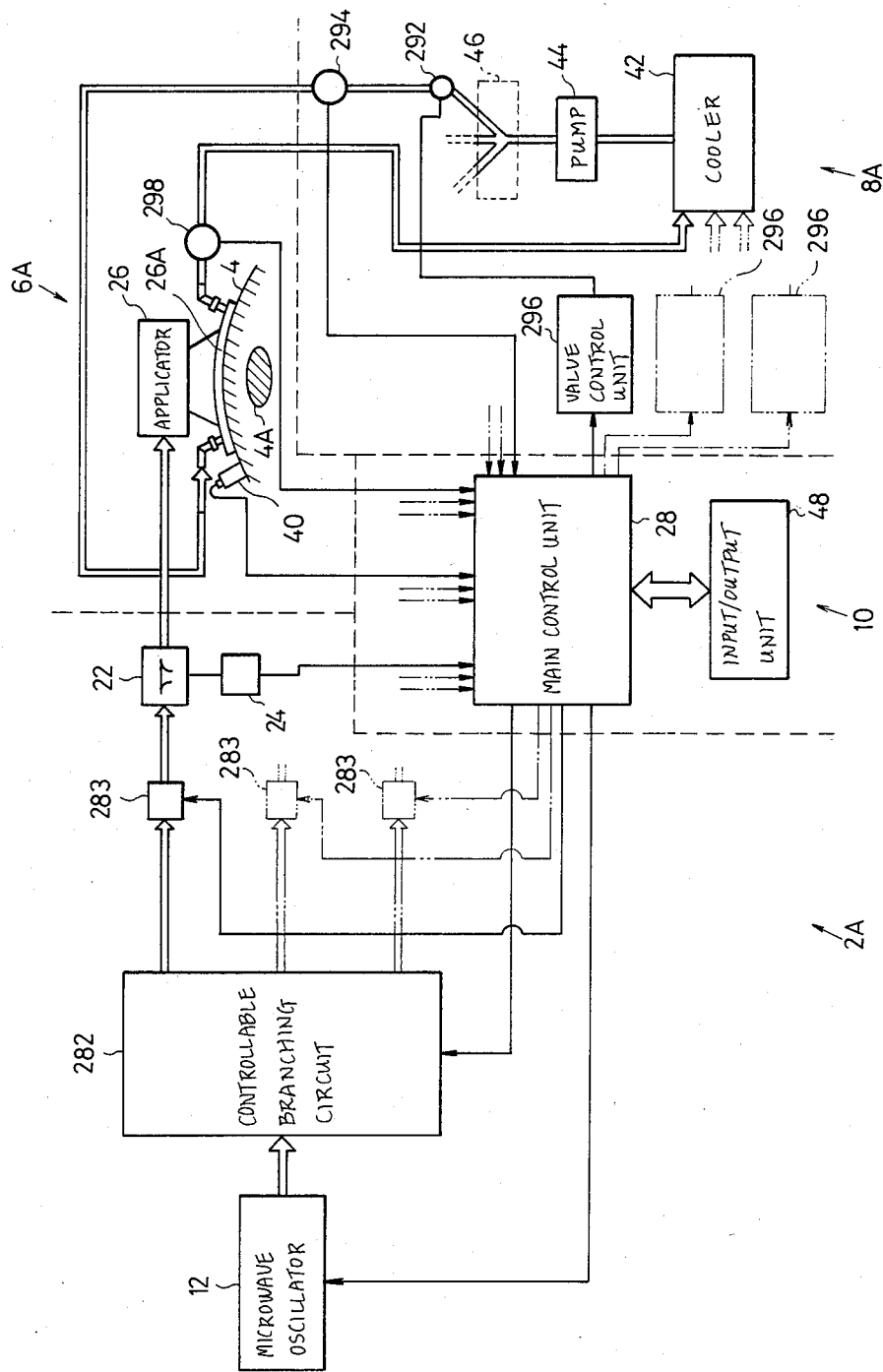
FIG. 19 is a general system diagram of a modification of the third embodiment of the invention.

A modification of the third embodiment is shown in FIG. 19. This modification employs the electromagnetic wave supply section 2A which is used in the second embodiment (see FIG. 15). The arrangement of the other portions of this modification is the same as that of the third embodiment. With this modification, it is also possible to obtain advantageous effects which are substantially equivalent to those offered by the third embodiment, and the arrangement of the electromagnetic wave supply section is further simplified.

It is to be noted that either the cancerous cell temperature sensors 40 or the coolant temperature sensors 298 may be omitted in accordance with need in the arrangement shown in FIG. 16 which illustrates the third embodiment and the arrangement shown in FIG. 19 which illustrates the modification of the third embodiment.

Fourth embodiment:

A fourth embodiment of the invention will now be described with reference to FIGS. 20 to 22.

This embodiment aims at accomplishing an object which is similar to that of the third embodiment. To this end, according to this embodiment, the temperature of cooling water itself is controlled.

Figure 20:
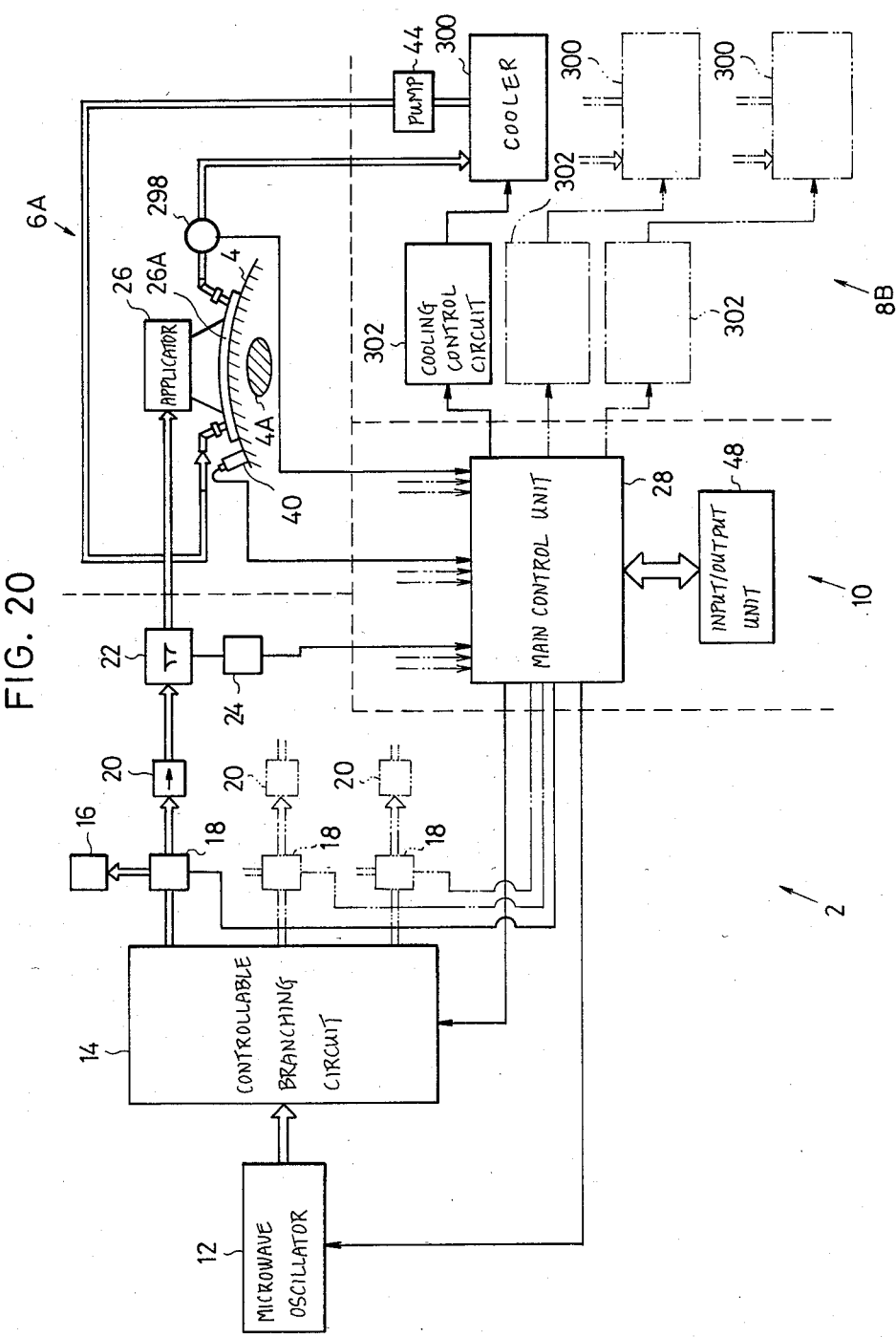
FIG. 20 is a general system diagram of a fourth embodiment of the invention.

Referring first to FIG. 20, the coolant supply section 8B of the fourth embodiment is provided with coolers 300 each of which cools the coolant supplied to the corresponding one of the three patients, and cooling control circuits 302 each controlling the corresponding cooler 300 such as to adjust the temperature of the coolant, thus constituting a cooling system for each patient.

The arrangement of the other portions is the same as that of the third embodiment.

Accordingly, in this case, information about the temperature of the hyperthermia treatment region of each body 4 is delivered to the main control unit 28 from the corresponding cancerous cell temperature sensor 40 and the corresponding coolant temperature sensor 298 which in combination serve as a heated region temperature detecting means. The main control unit 28 comprehensively makes a dicision on the basis of the basis of the thus delivered temperature information and instruction information input by the operator when controlling the switching operation of each of the coaxial switches 18, and delivers a control signal to each of the cooling control circuits 302. In response to this control signal, each cooling control circuit 302 controls the corresponding cooler 300, thereby properly varying the temperature of the cooling water.

The general operation of the fourth embodiment will now be explained. In this case, it is assumed that a target value for the cancerous cell temperature is set at 43.5° C., while a target value for the surface temperature is set at 20° C.

Figure 21:
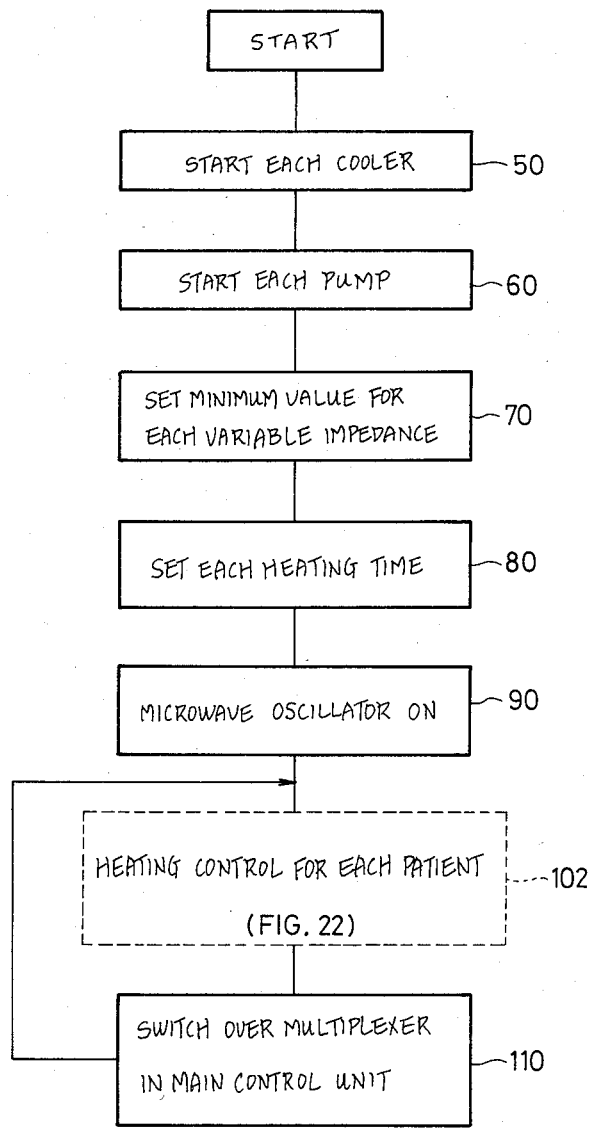
FIGS. 21 and 22 are flow charts which show the operation of the embodiment illustrated in FIG. 20.

First, each cooler 300 is started (Step 50 in FIG. 21), and each pump 44 is started (Step 60 in FIG. 21). Then, a minimum value for each of the variable impedances in the controllable branching circuit 14 is set (Step 70 in FIG. 21), a heating time for each patient is set (Step 80 in FIG. 21), and the microwave oscillator 12 is turned ON (Step 90 in FIG. 21). Thereafter, the heating control for each patient is effected (Steps 102 and 110 in FIG. 21) by time-division multiplexing (see FIG. 7).

Figure 22:
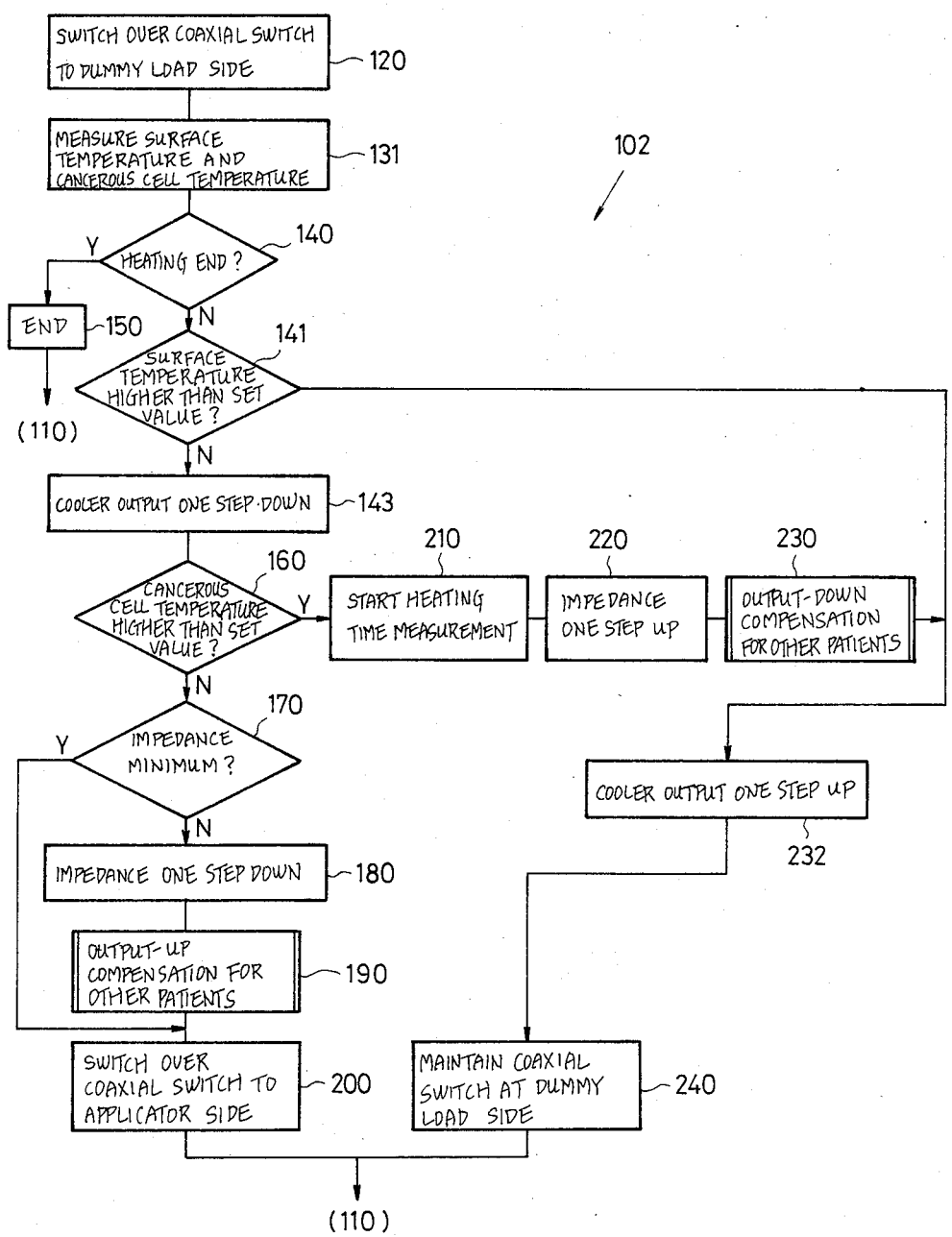

FIG. 22 shows in detail a flow chart for the control which is effected for each patient and which is shown in Step 102 in FIG. 21. According to the flow chart shown in FIG. 22, after a judgement (Step 141 in FIG. 22) has been made as to whether or not the surface temperature is higher than the set value, a cooling control is effected in such a manner that the output (cooling capacity) of the cooler 300 is stepped down (Step 143 in FIG. 22) or up (Step 232 in FIG. 22) by one degree. The other control operations of this embodiment are the same as those shown in FIG. 18 which illustrates the operation of the third embodiment. The reason why the cooling capacity is stepped down or up by one degree in the above-described control is the same as that in the case of the third embodiment in which the valve 292 is closed or opened by one step. Accordingly, this embodiment also has heating characteristics which are similar to those described above.

Thus, it is possible according to the fourth embodiment to obtain advantageous effects which are substantially equivalent to those which are offered by the third embodiment. In addition, since the coolant paths are independently arranged for individual patients, there is not interference between the coolant paths, which fact advantageously stabilizes the cooling control.

Figure 23:
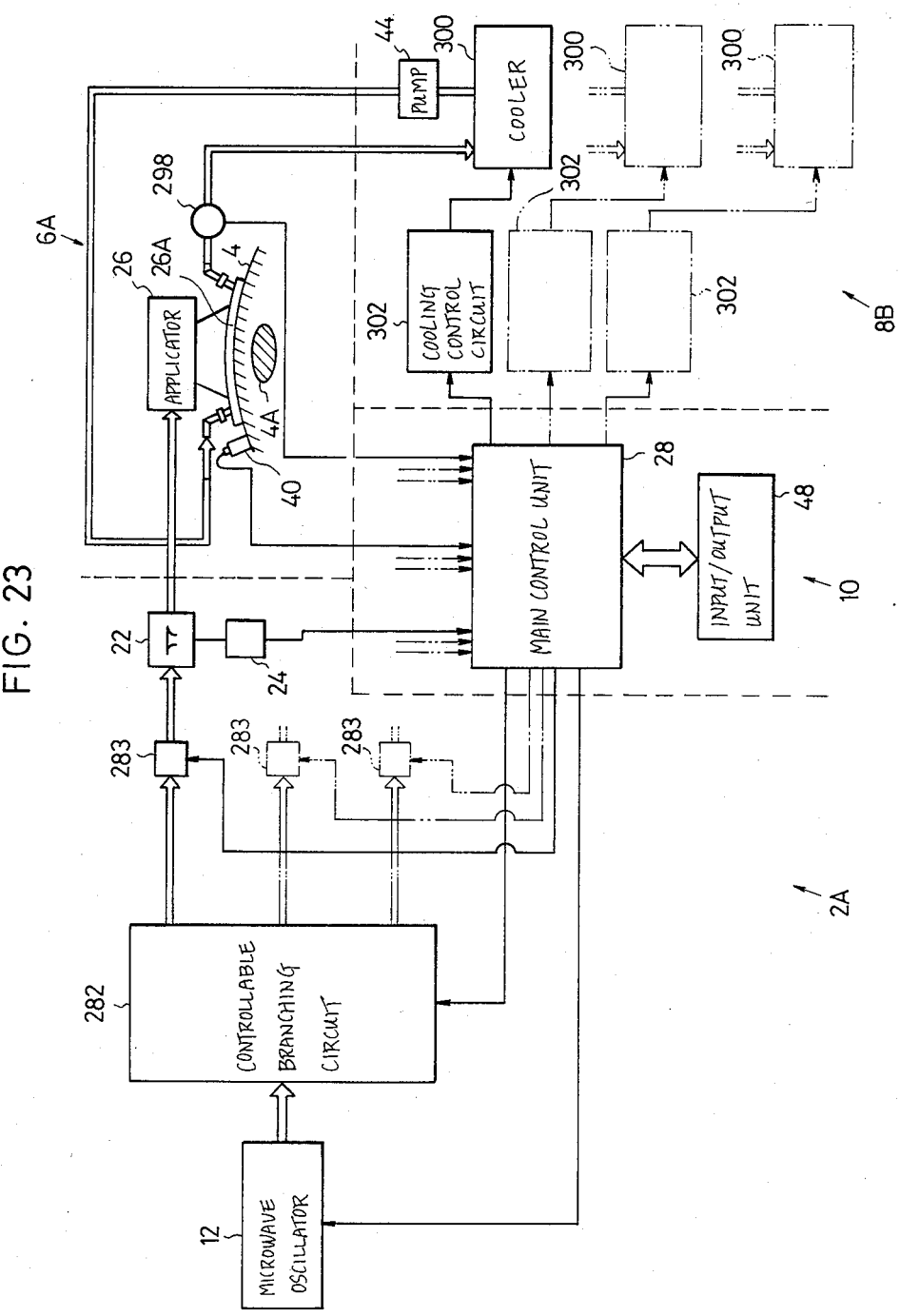
FIG. 23 is a general system diagram of a modification of the fourth embodiment.

A modification of the fourth embodiment is shown in FIG. 23. This modification employs the electromagnetic wave supply section 2A which is used in the second embodiment (see FIG. 15). The arrangement of the other portions of this modification is the same as that of the fourth embodiment. With this modification, it is also possible to obtain advantageous effects which are substantially equivalent to those which are offered by the fourth embodiment, and the arrangement of the electromagnetic wave supply section is further simplified.

It is to be noted that either the cancerous cell temperature sensors 40 or the coolant temperature sensors 298 may be omitted in accordance with need in the arrangement shown in FIG. 20 which illustrates the fourth embodiment and in the arrangement shown in FIG. 23 which illustrates the modification of the fourth embodiment.

Figure 24:
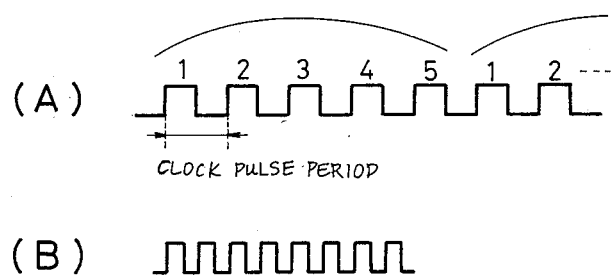
FIGS. 24(A) and 24(B) are timing charts which respectively show other examples of a clock pulse train.

It is to be noted also that, although the number of patients who are subjected to hyperthermia treatment is three in each of the above-described embodiments, the number of patients may be increased. In such a case (e.g., where the number of patients is five), it is only necessary to change the clock pulse train shown in FIG. 7 into one such as that shown in FIG. 24(A). By controlling or varying the period of this clock pulse train, it is possible to determine a microwave irradiation period which is defined between two adjacent cancerous cell temperature measuring periods. Accordingly, if the period of the clock pulse train is reduced in such a manner as that shown in FIG. 24(B), the microwave irradiation interval is reduced correspondingly. It is therefore possible for a increased number of patients to be simultaneously subjected to hyperthermia treatment. Even in such a case, no problem is experienced with the treatment since the cancerous cell temperature measuring period ($\Delta h$) is also extremely short and therefore ignorable for practical purposes. When the number of patients is increased, it is only necessary to correspondingly increase the number of branched output terminals of the branching circuit 14. Additionally, in place of the isolators 20 shown in FIGS. 1, 16 and 20, combinations of circulators and dummy loads may be employed to prevent any reflected waves from undesirably entering the branching circuit 14. Further, the microwave oscillator 12 may be controlled by employing an inverter.

What is claimed is:

1. Hyperthermia apparatus comprising:
    (a) a microwave oscillator for generating microwaves;
    (b) a branching circuit connected to said oscillator for dividing the generated microwaves into a plurality of branches, each branch having controllable impedance means for establishing the power level in the branch in response to a power level control signal;
    (c) an applicator associated with each branch for applying microwaves therein to a treatment region of a patient; and
    (d) a main control unit comprising means for producing power level control signals that are supplied to said branching circuit such that a change in the impedance of the controllable impedance means in one branch automatically produces compensating changes in the impedances of the controllable impedance means in the other branches, said compensating changes minimizing changes in the power level of said other branches and response to a change in the power level of said one branch.

2. Hyperthermia apparatus in accordance with claim 1 wherein each branch includes measn for producing a representation of the reflection coefficient of microwaves in the branch, said main control unit being constructed and arranged to produce power level control signals for each branch functionally related to the reflection coefficient in the branch.

3. Hyperthermia apparatus in accordance with claim 2 wherein said means for producing a representation of the reflection coefficient in a branch comprises a directional coupler for coupling the microwaves in the branch to the applicator therein, and a detector connected to the coupler for producing an output representative of the reflection coefficient in the branch.

4. Hyperthermia apparatus in accordance with claim 1 wherein said branching circuit includes a power divider circuit for each branch, and a dummy load capable of absorbing microwave power without reflection, said branching circuit being constructed and arranged such that the power divider circuits are connected serially between the oscillator and the dummy load.

5. Hyperthermia apparatus in accordance with claim 4 wherein the controllable impedance means in each branch establishes the portion of power that the power divider passes into a branch, and the portion passed to a downstream power divider.

6. Hyperthermia apparatus in accordance with claim 1 wherein each branch includes a surface temperature sensor, a cooling mechanism for cooling the surface of the patient being treated by microwaves applied to the patient by the applicator of the branch, and cooling control means for controlling the level of cooling effected by the cooling mechanism, said control unit including means for causing the cooling control means of a branch to incrementally change the amount of cooling effected by the cooling mechanism when the surface temperature sensor senses a temperature different from a set value.

7. Hyperthermia apparatus according to claim 6 wherein each branch includes a cell temperature sensor, and said main contorl unit includes means for changing the power level control signal for the controllable impedance mean in the branch such that the controllable impedance means is incrementally decreased or increased when the cell temperature sensor senses a temperature respectively greater or less than a set value.

8. Hyperthermia apparatus acoording to claim 7 wherein each branch includes means responsive to a decrease or increase in the controllable impedance means in the other branches such that the power levels therein remain substantially unaffected.

9. A heating apparatus for hyperthermia comprising:
    a single electromagnetic wave generating means;
    a plurality of applicators, each of which irradiates a given hyperthermia treatment region of a living body with electromagnetic waves outputtted from said electromagnetic wave generating means;
    variable electromagnetic wave branching means provided between said electromagnetic wave generating means and said plurality of applicators, wherein said branching means comprises a plurality of output terminals, wherein said branching means is adapted to branch electromagnetic waves outputted from said electromagnetic wave generating means to said plurality of electromagnetic wave output terminals and to enable adjustment of the output level of each of said branched electromagnetic waves;
    a plurality of switching means, each of which selectively connects one applicator to a different output terminal of said variable electromagnetic wave branching means so as to enable the course of electromagnetic waves to be switched over to said applicators;
    a plurality of cooling mechanisms respectively provided on said applicators for cooling the body surfaces to which said applicators apply said electromagnetic waves, wherein said cooling mechanisms comprise a coolant passing through each of said cooling mechanisms;
    heated region temperature detecting means respectively provided for each of said applicators, each of said detecting means being adapted to detect the temperatrue of the hyperthermia treatment region which is irradiated with electromagnetic waves by one of said applicators, wherein said detecting means comprises means for detecting the temperature of said coolant and the surface of said region; and
    a main control unit comprising means for controlling the switching operation of each of said electromagnetic wave switching means and for controlling the output level of each of the electromagnetic waves branched off by said variable electromagnetic wave branching means to a prdetermined value as a function of an output signal from the corresponding heated region temperature detecting means.

10. A heated apparatus for hyperthermia according to claim 9, wherein each of said switching means has a dummy load connected to one of its output terminals.

11. A heating apparatus for hyperthermia according to claim 9, wherein each of said switching means is adapted to switch over the course of electromagnetic waves by an ON/OFF switching operation.

12. A heating apparatus for hyperthermia according to claim 9, wherein each of said heated region temperature detecting means further comprises a cancerous cell temperature sensor which detects the temperature of cancerous cells within a living body at a hyperthermia treatment region.

13. A heating apparatus for hyperthermia according to claim 9, wherein said surface temperature sensing means comprises means for indirectly detecting the temperature of the surface of said living body at a hyperthermia treatment region by sensing said coolant leaving said surface.

14. A heating apparatus for hyperthermia according to claim 9, wherein each of said cooling mechanisms comprises means for adjusting the cooling capacity of said cooling mechanism by individually controlling the flow rate of the coolant supplied to each of said cooling mechanisms.

15. A heating apparatus for hyperthermia according to claim 9, wherien said cooling mechanisms comprise means for adjusting by individually controlling the temperature of the coolant supplied to each of said cooling mechanisms.

* * * * *